United States Patent
Stewart

(10) Patent No.: US 9,173,971 B2
(45) Date of Patent: Nov. 3, 2015

(54) SIMPLE ADHESIVE COACERVATES AND METHODS OF MAKING AND USING THEREOF

(75) Inventor: Russell J. Stewart, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 302 days.

(21) Appl. No.: 13/295,061

(22) Filed: Nov. 12, 2011

(65) Prior Publication Data

US 2012/0177918 A1 Jul. 12, 2012

Related U.S. Application Data

(60) Provisional application No. 61/412,834, filed on Nov. 12, 2010.

(51) Int. Cl.
*A61L 24/00* (2006.01)

(52) U.S. Cl.
CPC .......... *A61L 24/001* (2013.01); *Y10T 428/2852* (2015.01)

(58) Field of Classification Search
None
See application file for complete search history.

(56) References Cited

U.S. PATENT DOCUMENTS

| | | | |
|---|---|---|---|
| 3,458,460 A | 7/1969 | Shepard et al. | |
| 3,947,396 A | 3/1976 | Kangas et al. | |
| 3,950,296 A | 4/1976 | Kangas et al. | |
| 4,767,463 A | 8/1988 | Brode et al. | |
| 4,913,743 A | 4/1990 | Brode et al. | |
| 5,529,914 A | 6/1996 | Hubbell et al. | |
| 6,312,725 B1 | 11/2001 | Wallace et al. | |
| 6,428,978 B1 | 8/2002 | Olsen et al. | |
| 6,497,729 B1* | 12/2002 | Moussy et al. | 623/23.57 |
| 6,568,398 B2 | 5/2003 | Cohen | |
| 6,916,488 B1 | 7/2005 | Meier et al. | |
| 7,622,533 B2 | 11/2009 | Lee | |
| 8,283,384 B2* | 10/2012 | Stewart et al. | 514/772.1 |
| 2001/0056301 A1 | 12/2001 | Goupil et al. | |

(Continued)

FOREIGN PATENT DOCUMENTS

| | | |
|---|---|---|
| CN | 1341032 | 3/2002 |
| CN | 1446590 | 10/2003 |

(Continued)

OTHER PUBLICATIONS

Rapid Gel Formation and Adhesion in Photocurable and Biodegradable Block Copolymers with High DOPA Content, Lee et al., Macromolecules 206, 39, 1740-1748.*

(Continued)

*Primary Examiner* — James J Seidleck
*Assistant Examiner* — Peter A Salamon
(74) *Attorney, Agent, or Firm* — Gardner Groff Greenwald & Villanueva, PC

(57) ABSTRACT

Described herein is the synthesis of adhesive from simple adhesive coacervates and their uses thereof. The adhesives are produced by (a) preparing a solution comprising (1) a polyelectrolyte, wherein the polyelectrolyte comprises a polyanion or polycation but not a combination thereof, the polyeletrolyte comprises at least one crosslinking group, and (2) a sufficient amount of a complimentary counterion to produce a simple adhesive coacervate; and (b) crosslinking the simple adhesive coacervate to produce the adhesive. The adhesives have numerous medical and non-medical applications.

27 Claims, 9 Drawing Sheets

(56) References Cited

U.S. PATENT DOCUMENTS

| | | | |
|---|---|---|---|
| 2002/0006886 | A1 | 1/2002 | Beerse et al. |
| 2002/0164364 | A1 | 11/2002 | Quong |
| 2002/0169476 | A1 | 11/2002 | Cohen |
| 2003/0023000 | A1 | 1/2003 | Bavouzet et al. |
| 2004/0013738 | A1 | 1/2004 | Voigt et al. |
| 2004/0086479 | A1 | 5/2004 | Grinstaff et al. |
| 2005/0020734 | A1 | 1/2005 | Asgarzadeh et al. |
| 2005/0147580 | A1 | 7/2005 | Connor et al. |
| 2005/0220751 | A1 | 10/2005 | Charmot et al. |
| 2005/0281883 | A1 | 12/2005 | Daniloff et al. |
| 2006/0007528 | A1 | 1/2006 | Cao et al. |
| 2006/0015083 | A1 | 1/2006 | Munro et al. |
| 2006/0039950 | A1 | 2/2006 | Zhou et al. |
| 2006/0116682 | A1 | 6/2006 | Longo |
| 2006/0122290 | A1* | 6/2006 | Hubbell et al. ............... 523/113 |
| 2006/0156954 | A1 | 7/2006 | Li et al. |
| 2006/0183848 | A1 | 8/2006 | Maier et al. |
| 2006/0240064 | A9 | 10/2006 | Hunter et al. |
| 2006/0241242 | A1 | 10/2006 | Devlin |
| 2006/0275337 | A1 | 12/2006 | Cohen Stuart et al. |
| 2006/0276371 | A1 | 12/2006 | Schreiner et al. |
| 2007/0020469 | A1 | 1/2007 | Wood et al. |
| 2007/0077276 | A1 | 4/2007 | Haynie |
| 2007/0085059 | A1 | 4/2007 | Mora-Gutierrez et al. |
| 2007/0191273 | A1 | 8/2007 | Ambati et al. |
| 2007/0196454 | A1 | 8/2007 | Stockman et al. |
| 2008/0003288 | A1 | 1/2008 | Bromberg et al. |
| 2008/0075778 | A1 | 3/2008 | Heller |
| 2009/0162407 | A1 | 6/2009 | Biggs et al. |
| 2010/0056474 | A1 | 3/2010 | Baker et al. |
| 2010/0120923 | A1* | 5/2010 | Stewart et al. ............. 514/772.1 |
| 2010/0291169 | A1 | 11/2010 | Toreki et al. |
| 2010/0305626 | A1 | 12/2010 | Stewart et al. |
| 2011/0054392 | A1 | 3/2011 | Nies |
| 2011/0287067 | A1 | 11/2011 | Stewart |
| 2011/0288274 | A1 | 11/2011 | Russell et al. |
| 2013/0129787 | A1 | 5/2013 | Stewart |
| 2013/0189313 | A1 | 7/2013 | Stewart |
| 2014/0287061 | A1 | 9/2014 | Landolina |

FOREIGN PATENT DOCUMENTS

| | | | |
|---|---|---|---|
| CN | 101405037 | | 4/2009 |
| EP | 0632329 | A1 | 1/1995 |
| JP | 2003280056 | | 12/1991 |
| JP | 2002166158 | | 6/2002 |
| JP | 2009084224 | | 4/2009 |
| JP | 2009084292 | | 4/2009 |
| WO | 9506056 | | 3/1995 |
| WO | 02092217 | | 11/2002 |
| WO | 02100453 | | 12/2002 |
| WO | WO 2005/019421 | A2 | 3/2005 |
| WO | WO-2007/024972 | A2 | 3/2007 |
| WO | WO-2007/030811 | A2 | 3/2007 |
| WO | WO 2009/094060 | A1 | 7/2009 |
| WO | WO 2009094060 | A1 * | 7/2009 ............... C08F 8/06 |
| WO | WO-2011/06595 | A1 | 1/2011 |
| WO | WO-2011/011658 | A1 | 1/2011 |
| WO | WO-2011/028967 | A1 | 3/2011 |
| WO | 2011149907 | | 12/2011 |
| WO | WO 2012/065148 | A2 | 5/2012 |
| WO | WO 2012/065148 | A3 | 5/2012 |

OTHER PUBLICATIONS

Dong Soo Hwang, et al., "Expression of Functional Recombinant Mussel Adhesive Protein Mgfp-5 in *Escherichia coli*," *Applied and Environmental Microbiology*, Jun. 2004; Copyright 2004, American Society for Microbiology; vol. 70, No. 6, pp. 3352-3359.
Miaoer Yu et al., "Synthetic Polypeptide Mimics of Marine Adhesives," *Macromolecules* 1998, 31: Copyright 1998, American Chemical Society; Published on Web Jul. 10, 1998; pp. 4739-4745.
Bruce P. Lee et al., "Rapid Gel Formation and Adhesion in Photocurable and Biodegradable Block Copolymers with High DOPA Content," *Macromolecules* 2006, 39; Copyright 2006, American Chemical Society; Published on Web Feb. 9, 2006; pp. 1740-1748.
International Search Report mailed on Jul. 5, 2012 for International Application No. PCT/US2011/060500, 5 pages.
Wang et al., "A novel bioadhesive protein of silk filaments spun underwater by caddisfly larvae", Adv. Mater. Res., 2009, vol. 79-82, pp. 1631-1634.
US Office Action for U.S. Appl. No. 13/580,794 dated May 12, 2015.
US Advisory Action for U.S. Appl. No. 13/114,397 dated Mar. 23, 2015.
US Office Action for U.S. Appl. No. 13/114,397 dated May 22, 2015.
Stewart et al., "The Tube Cement of Phragmatopoma Californica: A Solid Foam", The Journal of Experimental Biology, 2004, vol. 207, No. 26, pp. 4727-4734.
Chinese First Office Action in CN Patent Application 201080038397 issued Apr. 3, 2013; 7 pp. (English summary).
Chinese First Office Action in CN Patent Application 201180024981.8 issued Mar. 27, 2014; 9 pp. (English summary).
Chinese First Office Action in CN Patent Application 201180050846.0 issued Apr. 3, 2014; 7 pp. (English summary).
Chinese First Office Action in CN Patent Application No. 201180010546 issued on Aug. 13, 2013 (English translation).
Chinese Second Office Action in CN Patent Application 201080038397 issued Dec. 16, 2013; 4 pp.
Chinese Second Office Action in CN Patent Application No. 200880128307.2 issued on Apr. 1, 2011, pp. 9 (translation).
Chinese Second Office Action in CN Patent Application No. 201180010546 issued on Jul. 2, 2014 (English summary).
Chinese Third Office Action in CN Patent Application 201080038397 issued Aug. 21, 2014; 4 pp.
International Search Report mailed on Aug. 26, 2013 for International Application No. PCT/US2013/029131.
International Search Report mailed on May 7, 2012 for International Application No. PCT/US/2011/060500.
International Search Report mailed on Nov. 22, 2010, for Application No. PCT/US10/43009.
ISR and WO mailed on Jan. 6, 2009, for Application No. PCT/US08/083311.
Japanese First Office Action in JP Application No. 2012-521803 issued Aug. 6, 2014; 4 pp.
Japanese First Office Action in JP Application No. 2012-555168 issued Aug. 12, 2014; 2 pp.
Russian Office Action for Patent Application No. 2010135333/15(050196) dated Nov. 6, 2012 (translation).
Supplementary European Search Report for European Application No. 10802933.1 dated Jun. 24, 2014, pp. 11.
Written Opinion of the International Searching Authority issued in PCT/US2012/044299 dated Nov. 16, 2012.
US Advisory Action for U.S. Appl. No. 12/864,045 dated Sep. 23, 2014.
US Advisory Action for U.S. Appl. No. 13/617,882 dated Sep. 18, 2014.
US Office Action for U.S. Appl. No. 12/508,280 dated Sep. 20, 2011.
US Office Action for U.S. Appl. No. 12/864,045 dated Jun. 18, 2014.
US Office Action for U.S. Appl. No. 12/864,045 dated Oct. 7, 2013.
US Office Action for U.S. Appl. No. 13/114,397 dated Feb. 27, 2014.
US Office Action for U.S. Appl. No. 13/295,061 dated Mar. 4, 2014.
US Office Action for U.S. Appl. No. 13/580,794 dated Aug. 1, 2014.
US Office Action for U.S. Appl. No. 13/580,794 dated Jan. 10, 2014.
US Office Action for U.S. Appl. No. 13/617,882 dated Aug. 27, 2013.
US Office Action for U.S. Appl. No. 13/617,882 dated Jun. 5, 2014.
Berg et al., "The Thermal Transition of a Non-Hydroxulated Form of Coolagen. Evedence for a Role for Hydroxyproline in Stabilizing the Triple-Helix of Collagen", Biochem Biophys Res Commun, vol. 52, pp. 115-12, Mar. 12, 1973.
Chinese First Office Action in CN Patent Application No. 200680128307.2 issued on Oct. 27, 2011, pp. 13.
Kamachi et al. "Synthesis of Block Polmers for Desalination Membranes. Preparation of Block Coplymers of 2-Vinylpyridine and Methacrylic Acid or Acrylic Acid", Macromolecules, 1972, vol. 5, No. 2, pp. 161-168.

(56) References Cited

OTHER PUBLICATIONS

Kayitmazer et al., "Mesophase Separation and Probe Dynamics in Protein-Polyelectrolyte Coacervates", Chemical Engineering Faculty Publications, 2007, vol. 3, pp. 1064-1076.
Lee et al., "Single-Molecule Mechanics of Mussel Adhesion", PNAS, 2006, vol. 103, No. 35, pp. 12999-13003.
Lee et al., "Synthesis of 3,4-dihydropxyphenylalanine (DOPA) Containing Monomers and their Co-Polymerization with PEG-Diacrylate to form Hydrogels", J. Biomater. Sci. Polymer Edn., 2004, vol. 15, No. 4, pp. 449-464.
Lim et al., "The Adhesive Properties of Coacervated Recombinant Hybrid ussel", Biomaterials, 2010, vol. 31, No. 13, pp. 3715-3722.
Liu et al., "Chemistry of Periodate Mediated Cross-Linking of 3,4-Dihydroxlphenylalanine-Containing Molecules to Proteins", JACS, 2006, vol. 128, pp. 15228-15235.
PCT International Preliminary Report on Patentability for International Application No. PCT/US2008/083311, date of issuance Jul. 27, 2010, pp. 10.
PCT International Search Report for International Search Report and the Written Opinion of the International Searching Authority, or the Declaration for International Application No. PCT/US2011/037697, mailed on Sep. 13, 2011, pp. 9.
Shao et al. Macromolecules Bioscience, vol. 9, Issue 5, Published Online Nov. 28, 2008, pp. 464-471.
Stevens et al., "Multiscale Structure of the Underwater Adhesive of Phragmatopoma Californica: A Nanostructured Latex with a Steep Microporosity Gradient", Langmuir, 2007, vol. 23, pp. 5045-5049.
Supplementary Extended European Search Report for European Application No. 08871349.0 dated Nov. 14, 2011, pp. 4.
Written Opinion of the International Searching Authority issued in PCT/US2011/26169.
Zhao et al., "Cement Proteins of the Tube-Building Polychaete Phragmatopoma Californica", The Journal of Chemistry, 2005, vol. 280, No. 52, pp. 42938-42944.
Polyethyleneimine:EPOMIN, website, Nippon Shokubai, 2014.
Canadian Office Action for Application 2,712,843 dated Jul. 9, 2014.
Chinese Office Action for Application 201080038397.3 dated Sep. 11, 2014.
Chinese Office Action for Application 2012800362923 dated Jan. 7, 2015.
Notice of Preliminary Rejection from Korean Intellectual Property Office for Application 10-2010-7018637 dated Jan. 6, 2015.
Official Action for European Application 13 156 643.2-1302 dated Dec. 22, 2014.
US Advisory Action for U.S. Appl. No. 13/580,794 dated Nov. 13, 2014.
US Office Action for U.S. Appl. No. 12/864,045 dated Jan. 5, 2015.
US Office Action for U.S. Appl. No. 13/114,397 dated Oct. 23, 2014.
US Office Action for U.S. Appl. No. 13/295,061 dated Jan. 12, 2015.
US Office Action for U.S. Appl. No. 13/617,882 dated Nov. 19, 2014.
Supplementary European Search Report for EP Application No. 12804996 dated Feb. 19, 2015.
US Office Action for U.S. Appl. No. 13/617,882 dated Jun. 15, 2015.
Mo et al., "Soft tissue adhesive composed of modified gelatin and polysaccharides," J. Biomater. Sci. Polymer Edn., 2000, vol. 11, No. 4, pp. 341-351.
First Examination Report for Indian Application 1584/MUMNP/2010 dated May 15, 2015.

* cited by examiner

Pc-1:
MKVFIVLALVSAA YGCGVGIGC
AGGRCGGACG GKGYGYGG-K LGYGAYGKGG
IGGYGYGKGC VGGYGYGGLG AGK------
LGGYGYGGSK CGGYGYGGQK LGGYGYGGKK
LGGYGYAAKK VGGYGYGAKK VGGYGYGAKK
VGGYGYGAKK VGGYGYGAKK VGGYGYGAKK
VGGYGYGAKK VGGYGYGVKK VGGYGYG---

MW = 18,240
pI = 9.74

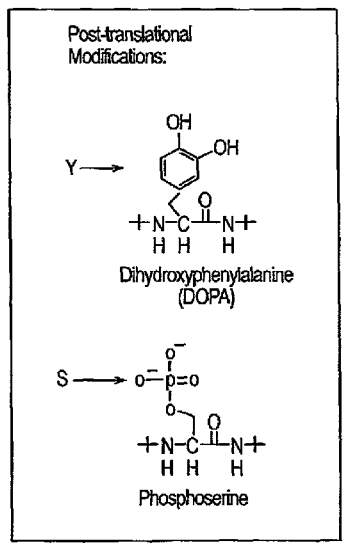

FIG. 2

Pc-2:
MKVLIFLATVAAVYG CGGGG WRSGSCGG
RWGHPAV----HKALGGYG-G
MGAHPAVHAAVHKALGGYGAGAYGAGA
WG-HPAV----HKALGGYGAGA
WG-HPAV----HKALGGYG-G
YGAHPAVHVAVHKALGGYGAGACGHKTGGYGG
YGAHP---VAV-KA--AY-NHGFNYGANNAIKSTKRFGG
YGAHP---V-VKKAFSRGLSHGAY-AG
SKAATGYGYGSGKAAGGYGY

MW = 21,116
pI = 9.91

Pc-3A:
MKLLSVFAIVVLAVYITHVEA
DSSSSSTSSSSSYSSSSSSSSSSSSYSSSSSYSSSSSS
SYSSSSSYSSSSSYSSSSYSSSSYSSSSSYSSSSILTSTS
SSDWKRKVPARRVLRTRRFLKCVTRCTLRCTLFRSAKT
CARKCSRRCLKRVF

MW = 13,979
pI = 2.5    polyphosphoserines

Pc-3H:
MKSFTIFAAILVALCYIQISEAG
CCKRYSSSYSSSSSSSSSSYSSSSSSSSSYSSSSSSSS
SYSSSSSSSSSSYSSSSSSYSSSSSSSYSSSSSSSSSS
YSSSSSYSSSSSSSSSSYSSSSSSSSYSSSSSSSSSSS
YSSSSSYSSSSSSSYSSSSSSSSSYSSSSSSYSSSS
SSSSSYSSSSSSSSSYSSSSSSSYSSSSSSYSSSSSSS
SSSSYSSSSSSSSSSYSSSSSSYSSSSSSSSSYSSSSS
SSSSYSSSSSSSSSSYSSSSSSSSSSYSSSSSSSYSSS
SSSSYSSSSSSSSSSYSSSSSSSYSSSSSSSSSSSYSS
SSSSSSSSSSYSSS
MW=30.525
pI=2.5

Pc-4: MW = 24,330 pI = 9.49
MPTLYKKVGKLVILAIIVTVASVASA
GYPTYSPSGGTHSGYNGPHGNVVKK
TYRGPYGAGAAK
AWNGYHGAGYTSVHHGPASTSWHTS
WSNKKGGYGYGLK
---NK-GYGYGLKKVGY
-GVGL-----HAAGW
HGVGPYGAGY--HGAGW
NGLGYHGAGYGV HGVGLHGAGYGL
HGVGLHGVGYGL HGVGLHGAGYGL
HGVGLHGVGYGL HGVGLHGAGYGI
HGVGLHGVGYGL HGVGLHGAGYGL
HGVGLHGVGYGL HGVGLHGAGCGIHKTACY
-GVGLHG-----HY

Pc-5: MW = 14,963 pI = 8.34
MKFLVLLALVASASA
YYPLMGGF
HGGWHAPMVHGGLY
HGGWHAPMVHGGLY
HGGWHAPIV
HGGWHAPVF
----HAPAPIHTVSHSVVN
---HVPMMPM
---WHHPAPAPAPAPRP
GRIILGGGKYGPFGKYGGG
AGLLALGALGGNGGFWKRR

Pc-6: MW = 37,763 pI = 8.25
METLFYNANFVQKSWLILLGLAAVVA
CSEYDKGLGGYGRPSYGGRRGYGGRRGLQYHGK
YQGRCEYDGLYFRDEKSFVYCSNRNSYIQPCAP
GTRNSPYTKYNRGSKYNYRDFCEFNLVDSGYVP
KPGYLPAPKKAYPTKVYDL
KVDYAP KVDYAP KVDYAP KVDYAP
KVDYAPKASVVPPKASYVDPTPTYGYEAPFK
GGYDKPSYGKDVDTSYESKTTYTVEKTAD
KGYGKGYGDKEISAKKSYTLTEKRDYDT
GYDNSRSDEDSKEY
GYDNDRSESYERTESYTDERTDGYGTQK
VEYTQQSEYDRVTRRGIWLHKGTEVEHVLY

Pc-7: MW = 15,073 pI = 8.50
MNTFVVIAAIVAVAA
CSGGYDGRQYTYRGR
YNNKCGNDGLYFKDDKNFXFCSN
GNSYVQPCAPGTRNS
GYNNYKQGSIYNYRDFCDVNLVDE
GYVGAKPGYNKGYNP
GYNPGYGGYNPGYST
GYGGYKAGPGPYW

Pc-8: MW = 16,772 pI = 10.29
MSNAFLXCQLCTKKLALILLVAVCAAVAVNA
CGPLGCS GGYGGVLK
CGVGGCALGGYGGGYSAGIGGYGIK
RLGCRGGRCGLRRRVGCRGGRCGLRG
RLGCRGGRCGLR KLGCRGGRCGLRG
RLGCRGGRCGLRKRLGCRGGR
GRGGYGGGYGGYVCSKGVCGGYPAYGK

FIG. 4

Protein Sequences
Amino Acid Mol %

| | Pc1 | Pc2 | Pc3a | Pc3b | Pc4 | Pc5 | Pc6 | Pc7 | Pc8 | Predicted* | Experimental† | |
|---|---|---|---|---|---|---|---|---|---|---|---|---|
| Ala (A) | 7.8 | 20.0 | 2.3 | 0.0 | 7.7 | 9.2 | 5.2 | 5.8 | 5.9 | 7.2 | 9.8 | |
| Arg (R) | 0.5 | 2.1 | 10.0 | 0.3 | 0.4 | 2.0 | 5.8 | 3.6 | 14.2 | 2.0 | 2.9 | (+) |
| Asn (N) | 0.0 | 2.1 | 0.0 | 0.0 | 2.4 | 1.4 | 3.0 | 11.7 | 1.2 | 1.0 | 2.8 | |
| Asp (D) | 0.0 | 0.0 | 1.5 | 0.0 | 0.0 | 0.0 | 8.2 | 5.1 | 0.0 | 0.2 | | |
| Cys (C) | 3.1 | 1.1 | 4.6 | 0.6 | 0.8 | 0.0 | 1.5 | 3.6 | 12.4 | 1.5 | 0.4 | N |
| Gln (Q) | 0.5 | 0.0 | 0.0 | 0.0 | 0.0 | 0.0 | 2.1 | 2.2 | 0.6 | 0.1 | 1.4 | |
| Glu (E) | 0.5 | 0.0 | 0.0 | 0.0 | 0.0 | 4.3 | 6.1 | 1.5 | 0.0 | 0.6 | | |
| Gly (G) | 41.7 | 27.4 | 0.0 | 0.0 | 33.7 | 20.6 | 9.7 | 18.2 | 32.5 | 20.0 | 26.2 | |
| His (H) | 0.0 | 8.9 | 0.0 | 0.0 | 12.6 | 11.3 | 0.9 | 0.0 | 0.0 | 5.3 | 3.5 | (+) N |
| Ile (I) | 1.6 | 0.5 | 1.5 | 0.0 | 1.6 | 2.8 | 1.2 | 1.5 | 1.2 | 1.1 | 0.6 | |
| Leu (L) | 3.6 | 3.2 | 4.6 | 0.0 | 7.7 | 5.7 | 4.2 | 2.2 | 11.8 | 3.8 | 3.4 | |
| Lys (K) | 13.5 | 6.8 | 4.6 | 0.3 | 4.1 | 2.1 | 9.4 | 5.1 | 4.7 | 4.8 | 4.4 | (+) N |
| Met (M) | 0.5 | 0.0 | 0.0 | 0.0 | 0.0 | 4.3 | 0.3 | 0.7 | 0.6 | 0.6 | | |
| Phe (F) | 0.5 | 1.6 | 2.3 | 0.0 | 0.0 | 2.8 | 1.8 | 3.6 | 0.6 | 0.9 | 1.1 | |
| Pro (P) | 0.0 | 3.7 | 0.8 | 0.0 | 2.4 | 11.3 | 6.1 | 5.8 | 1.2 | 2.5 | 2.7 | |
| Ser (S) | 1.0 | 3.7 | 51.5 | 88.1 | 3.3 | 1.4 | 7.0 | 4.4 | 2.4 | 30.1 | 28.5 | (−) |
| Thr (T) | 0.5 | 1.6 | 4.6 | 0.0 | 2.8 | 5.7 | 6.4 | 3.6 | 0.6 | 2.1 | 2.2 | |
| Trp (W) | 0.0 | 2.6 | 0.8 | 0.0 | 2.0 | 4.3 | 0.6 | 0.7 | 0.0 | 1.4 | | |
| Tyr (Y) | 17.2 | 8.9 | 7.7 | 10.7 | 10.6 | 4.3 | 13.6 | 14.6 | 4.7 | 10.3 | 6.1 | |
| Val (V) | 7.3 | 5.8 | 3.1 | 0.0 | 7.7 | 5.7 | 7.0 | 5.8 | 5.3 | 4.6 | 3.4 | |

\* Predicted mol% based on one copy of each of the five proteins.
† Experimental mol% from amino acid analysis of acid hydrolyzed glue.

(+) = positive charge
(−) = negative charge
N = nucleophilic

SIMPLE ADHESIVE COACERVATES AND METHODS OF MAKING AND USING THEREOF

CROSS REFERENCE TO RELATED APPLICATIONS

This application claims priority upon U.S. provisional application Ser. No. 61/412,834, filed Nov. 12, 2010. This application is hereby incorporated by reference in its entirety.

ACKNOWLEDGEMENTS

This invention was made with government support under N00014-10-1-0108 awarded by the Office of Naval Research. The government has certain rights in the invention.

CROSS REFERENCE TO SEQUENCE LISTING

Proteins described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

There has always been a need for the development of better adhesives, particularly adhesives that are exposed to aqueous environments. For example, adhesives that can be administered to a subject have numerous medical applications, such as with, bone fractures which are a serious health concern in society today. In addition to the fracture itself, a number of additional health risks are associated with the fracture. Intra-articular fractures are bony injuries that extend into a joint surface and fragment the cartilage surface. Fractures of the cartilage surface often lead to debilitating posttraumatic arthritis. Currently, stainless steel and titanium implants are the primary methods of fixation, but their size and the drilling necessary to place them frequently interfere with the exact manipulation and reduction of smaller pieces of bone and cartilage.

In additional to medical applications, adhesives that can be used or exposed to aqueous environments can have several beneficial applications in non-medical applications as well. For example, an adhesive can be used to help restore marine ecosystems by adhering coral and other materials to existing reefs to enhance the growth and development of the reef. Described herein are adhesives that address these needs.

SUMMARY

Described herein is the synthesis of adhesive from simple adhesive coacervates and their uses thereof. The adhesives are produced by (a) preparing a solution comprising (1) a polyelectrolyte, wherein the polyelectrolyte comprises a polyanion or polycation but not a combination thereof, the polyeletrolyte comprises at least one cros slinking group, and (2) a sufficient amount of a complimentary counterion to produce a simple adhesive coacervate; and (b) crosslinking the simple adhesive coacervate to produce the adhesive. The adhesives have numerous medical and non-medical applications. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIGS. 1-6 shows several protein sequences produced by *P. californica* that can be used as polycations in the present invention as well as synthetic polycations and polyanions useful in the present invention. FIG. 1 discloses "Pc-1" as SEQ. ID NO 1. FIG. 2 discloses "Pc-1," "Pc-2," "Pc-3A" and "Pc-3H" as SEQ ID NOS 1-3 and 10, respectively. FIG. 3 discloses "Pc-4" as SEQ ID NO 5. FIG. 4 discloses "Pc-4" "Pc-5," "Pc-6" "Pc-7" and "Pc-8" as SEQ ID NO 11 and 6-9, respectively. FIG. 6 discloses "Pc-3B" as SEQ ID NO 4.

FIG. 7 provides the amino acid mole % of Pc1-Pc8.

DETAILED DESCRIPTION

Figure 1:
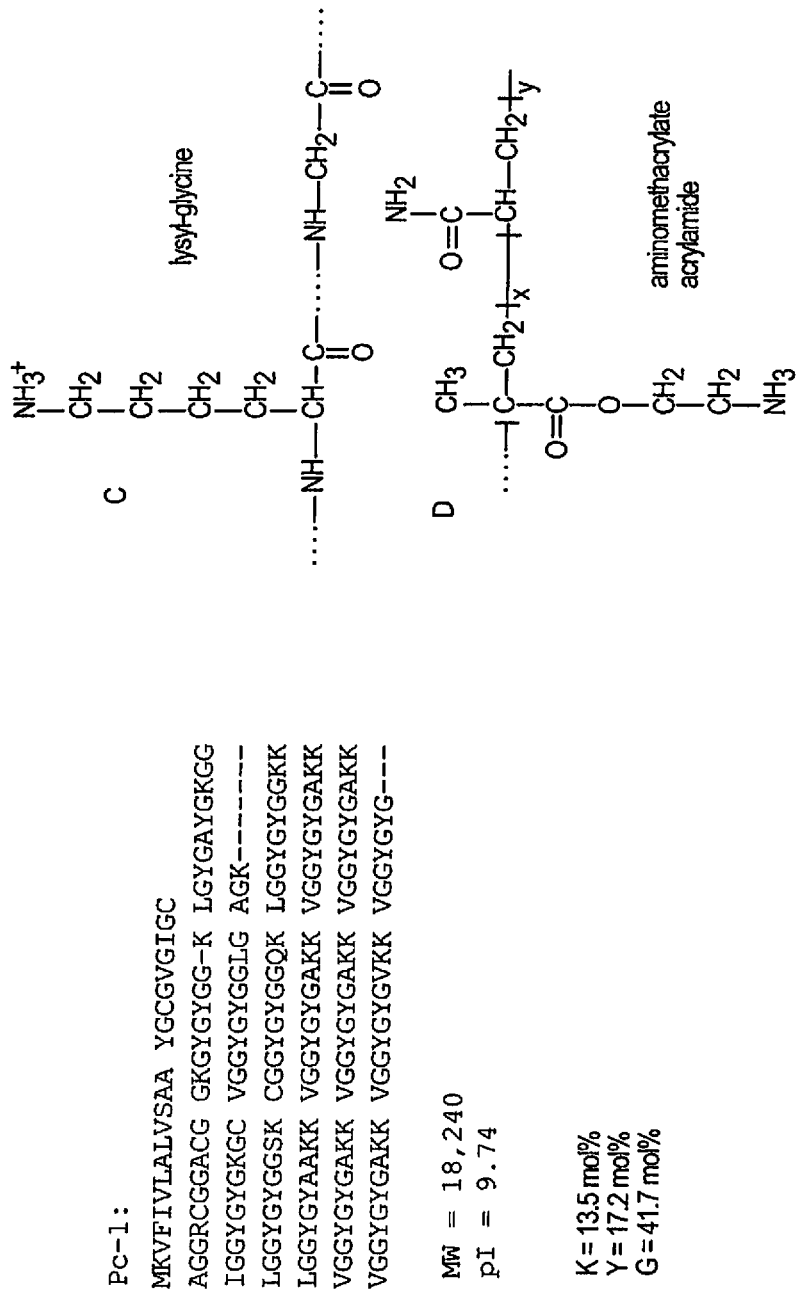

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$, $R^2$, $R^3$, $R^4$, $R^5$, $R^{13}$—$R^{22}$, $R^{30}$, $R^{40}$, $R^{41}$, A, X, Z, d, m, n, o, s, t, u, v, w, and x used throughout the application are the same variables as previously defined unless stated to the contrary.

The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, a palmitate group. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy.

Any of the compounds described herein can be the pharmaceutically-acceptable salt. In one aspect, pharmaceutically-acceptable salts are prepared by treating the free acid with an appropriate amount of a pharmaceutically-acceptable base. Representative pharmaceutically-acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

In another aspect, if the compound possesses a basic group, it can be protonated with an acid such as, for example, HCl, HBr, or $H_2SO_4$, to produce the cationic salt. In one aspect, the reaction of the compound with the acid or base is conducted in water, alone or in combination with an inert, water-miscible organic solvent, at a temperature of from about 0° C. to about 100° C. such as at room temperature. In certain aspects where applicable, the molar ratio of the compounds described herein to base used are chosen to provide the ratio desired for any particular salts. For preparing, for example, the ammonium salts of the free acid starting material, the starting material can be treated with approximately one equivalent of pharmaceutically-acceptable base to yield a neutral salt.

Described herein are adhesives produced from simple adhesive coacervate and their applications thereof. In general, the simple adhesive coacervates are a mixture of one or more polyelectrolytes (a polycation or a polyanion) capable of crosslinking with itself and one or more complimentary counterions in balanced proportions to produce stable aqueous coacervates at a desired pH. The simple adhesive coacervate is an associative liquid with a dynamic structure in which the individual polymer components diffuse throughout the entire phase. The adhesive complex coacervates exhibit low interfacial tension in water when applied to substrates either under water or that are wet. In other words, the simple adhesive coacervate spreads evenly over the interface rather than beading up. Upon crosslinking of the polyelectrolyte, the adhesive is produced.

In one aspect, the adhesive is produced by the process comprising:

(a) preparing a solution comprising (1) a polyelectrolyte, wherein the polyelectrolyte comprises a polyanion or polycation but not a combination thereof, the polyeletrolyte comprises at least one crosslinking group, and (2) a sufficient amount of a complimentary counterion to produce a simple adhesive coacervate; and (b) crosslinking the simple adhesive coacervate to produce the adhesive.

Each component of the coacervate and methods for making the same are described below.

The polyelectrolyte is composed of a polyanion or polycation but not a combination thereof. The term "polycation" is any polymer that has a net positive charge at the pH the simple adhesive coacervate is formed. Conversely, a "polyanion" is any polymer that has a net negative charge at the pH the simple adhesive coacervate is formed. Unlike a complex adhesive coacervate, which includes a polycation and polyanion, the simple adhesive coacervate useful herein includes only a polycation or a polyanion but not a combination thereof.

The polycation and polyanion are generally composed of a polymer backbone with a plurality of chargeable groups at a particular pH. The groups can be pendant to the polymer backbone and/or incorporated within the polymer backbone. In certain aspects, (e.g., biomedical applications), the polycation is any biocompatible polymer possessing cationic groups or groups that can be readily converted to cationic groups by adjusting the pH.

In one aspect, the polycation is a polyamine compound. The amino groups of the polyamine can be branched or part of the polymer backbone. The amino group can be a primary, secondary, or tertiary amino group that can be protonated to produce a cationic ammonium group at a selected pH. In general, the polyamine is a polymer with a large excess of positive charges relative to negative charges at the relevant pH, as reflected in its isoelectric point (pI), which is the pH at which the polymer has a net neutral charge. The number of amino groups present on the polycation ultimately determines the charge of the polycation at a particular pH. For example, the polycation can have from 10 to 90 mole %, 10 to 80 mole %, 10 to 70 mole %, 10 to 60 mole %, 10 to 50 mole %, 10 to 40 mole %, 10 to 30 mole %, or 10 to 20 mole % amino groups. As will be discussed below, additional amino groups can be incorporated into the polymer in order to increase the pI value. In general, the pI of the polycation is greater than the pH used to make the simple adhesive coacervate. In one aspect, the polycation has a pI value greater than 7.

In one aspect, the amino group can be derived from a residue of lysine, histidine, arginine, or imidazole attached to the polycation. Any anionic counterions can be used in association with the cationic polymers. The counterions should be physically and chemically compatible with the essential components of the composition and do not otherwise unduly impair product performance, stability or aesthetics. Non-limiting examples of such counterions include halides (e.g., chloride, fluoride, bromide, iodide), sulfate and methylsulfate.

In one aspect, the polycation is naturally-occurring polymer. For example, proteins produced by P. californica can be used as the polycation. FIGS. 1-6 show the protein sequences of several cement proteins produced by P. californica (Zhao et al. "Cement Proteins of the tube building polychaete Phragmatopoma californica" J. Biol. Chem. (2005) 280: 42938-42944). FIG. 7 provides the amino acid mole % of each protein. Referring to FIGS. 1-4, Pc1, Pc2, Pc4-Pc8 (SEQ ID NOS 1, 2, 5, 11 and 6-9, respectively) are polycations, where the polymers are cationic at neutral pH. The type and number of amino acids present in the protein can vary in order to achieve the desired solution properties. For example, referring to FIG. 7 Pc1 is enriched with lysine (13.5 mole %) while Pc4 and Pc5 are enriched with histidine (12.6 and 11.3 mole %, respectively).

After page 45 of the specification and immediately preceding the claims, please insert the written copy (sheets 1-18) of the sequence listing as appended to this Preliminary Amendment. The sequence listing in computer readable form (ASCII text file) is concurrently submitted herewith.

In another aspect, the polycation is a recombinant protein produced by artificial expression of a gene or a modified gene or a composite gene containing parts from several genes in a heterologous host such as, for example, bacteria, yeast, cows, goats, tobacco, and the like. In another aspect, the polycation can be a genetically modified protein.

In another aspect, the polycation can be a biodegradable polyamine. The biodegradable polyamine can be a synthetic polymer or naturally-occurring polymer. The mechanism by which the polyamine can degrade will vary depending upon the polyamine that is used. In the case of natural polymers, they are biodegradable because there are enzymes that can hydrolyze the polymers and break the polymer chain. For example, proteases can hydrolyze natural proteins like gelatin. In the case of synthetic biodegradable polyamines, they also possess chemically labile bonds. For example, β-aminoesters have hydrolyzable ester groups. In addition to the nature of the polyamine, other considerations such as the molecular weight of the polyamine and crosslink density of the adhesive can be varied in order to modify the degree of biodegradability.

In one aspect, the polycation includes a polysaccharide, a protein, a synthetic polyamine, or a synthetic polypeptide. Polysaccharides bearing one or more amino groups can be used herein. In one aspect, the polysaccharide is a natural polysaccharide such as chitosan. Similarly, the protein can be a synthetic or naturally-occurring compound. In another aspect, the biodegradable polyamine is a synthetic random copolypeptide, synthetic polyamine such as poly(β-aminoesters), polyester amines, poly(disulfide amines), mixed poly(ester and amide amines), and peptide crosslinked polyamines. It is desirable in certain aspects that the polycation as well as the polyanion be non-gelling and low-endotoxin.

In the case when the polycation is a synthetic polymer, a variety of different polymers can be used; however, in certain applications such as, for example, biomedical applications, it is desirable that the polymer be biocompatible and non-toxic to cells and tissue. In one aspect, the biodegradable polyamine can be an amine-modified natural polymer. The term "amine modified natural polymer" is defined as any natural polymer that has been subsequently manipulated or processed to change the natural state of the polymer. For example, the natural polymer can be chemically modified using the techniques described herein. Alternatively, the natural polymer can be denatured or digested by an enzyme. In one aspect, the amine-modified natural polymer can be an amine-modified protein such as, for example, gelatin or collagen modified with one or more alkylamino groups, heteroaryl groups, or an aromatic group substituted with one or more amino groups. Examples of alkylamino groups are depicted in Formulae IV-VI

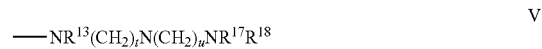

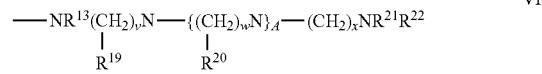

wherein $R^{13}$—$R^{22}$ are, independently, hydrogen, an alkyl group, or a nitrogen containing substituent;

s, t, u, v, w, and x are an integer from 1 to 10; and

A is an integer from 1 to 50, where the alkylamino group is covalently attached to the natural polymer. In one aspect, if the natural polymer has a carboxyl group (e.g., acid or ester), the carboxyl group can be reacted with a polyamine compound to produce an amide bond and incorporate the alkylamino group into the polymer. Thus, referring to formulae IV-VI, the amino group $NR^{13}$ is covalently attached to the carbonyl group of the natural polymer.

As shown in formula IV-VI, the number of amino groups can vary. In one aspect, the alkylamino group is —$NHCH_2NH_2$, —$NHCH_2CH_2NH_2$, —$NHCH_2CH_2CH_2NH_2$, —$NHCH_2CH_2CH_2CH_2NH_2$, —$NHCH_2CH_2CH_2CH_2CH_2NH_2$, —$NHCH_2NHCH_2CH_2CH_2NH_2$, —$NHCH_2CH_2NHCH_2CH_2CH_2NH_2$, —$NHCH_2CH_2CH_2NHCH_2CH_2CH_2CH_2NHCH_2CH_2CH_2NH_2$, —$NHCH_2CH_2NHCH_2CH_2CH_2CH_2NH_2$, —$NHCH_2CH_2NHCH_2CH_2CH_2NHCH_2CH_2CH_2NH_2$, or —$NHCH_2CH_2NH(CH_2CH_2NH)_dCH_2CH_2NH_2$, where d is from 0 to 50.

In one aspect, the amine-modified natural polymer can include an aryl group having one or more amino groups directly or indirectly attached to the aromatic group. Alternatively, the amino group can be incorporated in the aromatic ring. For example, the aromatic amino group is a pyrrole, an isopyrrole, a pyrazole, imidazole, a triazole, or an indole. In another aspect, the aromatic amino group includes the isoimidazole group present in histidine. In another aspect, the biodegradable polyamine can be gelatin modified with ethylenediamine.

In one aspect, the polycation includes a polyacrylate having one or more pendant amino groups. For example, the backbone can be a homopolymer or copolymer derived from the polymerization of acrylate monomers including, but not limited to, acrylates, methacrylates, acrylamides, and the like. In one aspect, the backbone of the polycation is polyacrylamide. In other aspects, the polycation is a block co-polymer, where segments or portions of the co-polymer possess cationic groups depending upon the selection of the monomers used to produce the co-polymer.

In one aspect, the polycation is a polyamino compound. In another aspect, the polyamino compound has 10 to 90 mole % tertiary amino groups. In a further aspect, the polycation polymer has at least one fragment of the formula I

Figure 3:
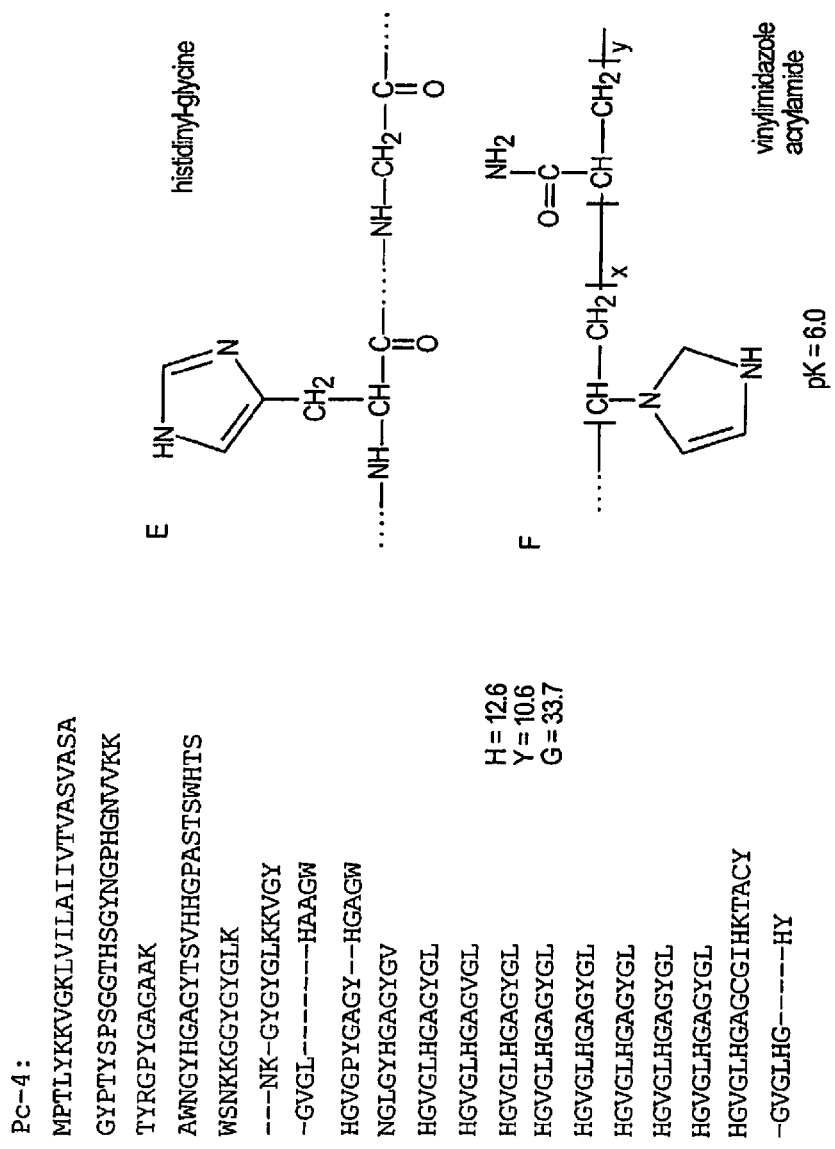
Figures 5A, 5B, 5C, 5D:
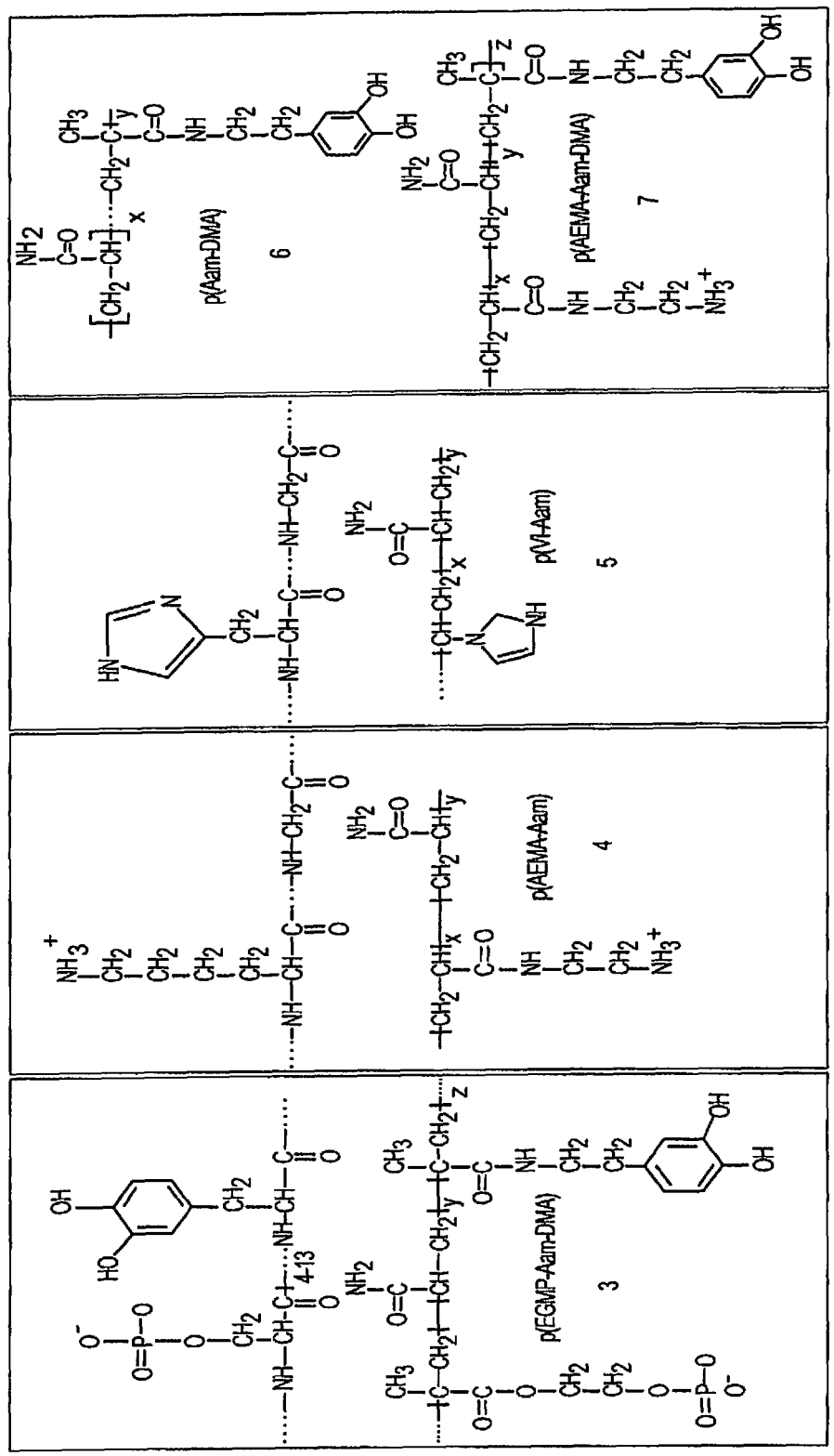

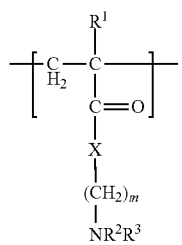

wherein $R^1$, $R^2$, and $R^3$ are, independently, hydrogen or an alkyl group, X is oxygen or $NR^5$, where $R^5$ is hydrogen or an alkyl group, and m is from 1 to 10, or the pharmaceutically-acceptable salt thereof. In another aspect, $R^1$, $R^2$, and $R^3$ are methyl and m is 2. Referring to formula I, the polymer backbone is composed of $CH_2$—$CR^1$ units with pendant —C(O)X$(CH_2)_m NR^2R^3$ units. In this aspect, the fragment having the formula I is a residue of an acrylate, methacrylate, acrylamide, or methacrylamide. FIG. 2 (structures C and D) and FIGS. 5 (4 and 7) show examples of polycations having the fragment of formula I, where the polymer backbone is derived from acrylamide and methacrylate residues as discussed above. In one aspect, the polycation is the free radical polymerization product of a cationic tertiary amine monomer (2-dimethylamino-ethyl methacrylate) and acrylamide, where the molecular weight is from 10 to 20 kd and possesses tertiary monomer concentrations from 15 to 30 mol %. FIG. 3 (structures E and F) and FIG. 5 (5) provide examples of polycations useful herein, where imidazole groups are directly attached to the polymer backbone (structure F) or indirectly attached to the polymer backbone via a linker (structure E via a methylene linker).

Similar to the polycation, the polyanion can be a synthetic polymer or naturally-occurring. When the polyanion is a synthetic polymer, it is generally any polymer possessing anionic groups or groups that can be readily converted to anionic groups by adjusting the pH. Examples of groups that can be converted to anionic groups include, but are not limited to, carboxylate, sulfonate, phosphonate, boronate, sulfate, borate, or a substituted or unsubstituted phosphate. The term "substituted phosphate" is defined herein as a phosphate group where one of the OH protons is substituted with an organic group such as, for example, an alkyl or aryl group. Any cationic counterions can be used in association with the anionic polymers if the considerations discussed above are met. Depending upon the selection of the anionic group, the group can be pendant to the polymer backbone and/or incorporated in the polymer backbone.

In one aspect, the polyanion is a polysaccharide. Examples of polysaccharides useful herein include, but are not limited to, a hyaluronate, arabic gum, an alginate, chondroitin sulfate, dermatan, dermatan sulfate, heparan sulfate, or any combination thereof. In another aspect, the polyanion comprises a polysaccharide, a protein, or a synthetic polypeptide.

In one aspect, the polyanion is a polyphosphate. In another aspect, the polyanion is a polyphosphate compound having from 10 to 90 mole % phosphate groups. For example, the polyphosphate can be a naturally-occurring compound such as, for example, highly phosphorylated proteins like phosvitin (an egg protein), dentin (a natural tooth phosphoprotein), casein (a phosphorylated milk protein), bone proteins (e.g. osteopontin), or DNA. In another aspect, the polyphosphate is an inorganic polyphosphate such as, for example, sodium polymetaphosphate (Graham's salt).

In other aspects, phosphorous containing polymers can be converted to polyanions. For example, a phospholipid or phosphosugar is not a polyanion but it can be converted into a polyanion by creating a liposome or a micelle with it. Thus, in this aspect, the complex coacervate is a charged colloid. Alternatively, the colloid can be produced by any of the polyanions or polycations described herein.

In another aspect, the polyphosphate can be a synthetic compound. For example, the polyphosphate can be a polymer with pendant phosphate groups attached to the polymer backbone and/or present in the polymer backbone. (e.g., a phosphodiester backbone). In one aspect, the polyphosphate can be produced by chemically or enzymatically phosphorylating a natural compound. In another aspect, a natural serine-rich protein can be phosphorylated to incorporate phosphate groups into the protein. In a further aspect, hydroxyl groups present on a polysaccharide can be phosphorylated to produce a polyanion useful herein.

In one aspect, the polyanion includes a polyacrylate having one or more pendant phosphate groups. For example, the backbone can be a homopolymer or copolymer derived from the polymerization of acrylate monomers including, but not limited to, acrylates, methacrylates, acrylamides, and the like. In one aspect, the backbone of the polyanion is derived from the polymerization of polyacrylamide. In other aspects, the polyanion is a block co-polymer, where segments or portions of the co-polymer possess anionic groups depending upon the selection of the monomers used to produce the co-polymer. In a further aspect, the polyanion can be heparin sulfate, hyaluronic acid, chitosan, and other biocompatible and biodegradable polymers typically used in the art.

In another aspect, the polyanion is a polymer having at least one fragment having the formula X

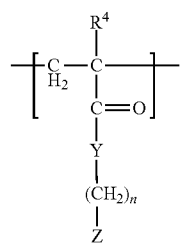

wherein $R^4$ is hydrogen or an alkyl group;
n is from 1 to 10;
Y is oxygen, sulfur, or $NR^{30}$, wherein $R^{30}$ is hydrogen, an alkyl group, or an aryl group;
Z is an anionic group or a group that can be converted to an anionic group, or the pharmaceutically-acceptable salt thereof.

In one aspect, Z is sulfate, sulfonate, carboxylate, borate, boronate, a substituted or unsubstituted phosphate, or a phosphonate.

In one aspect, the polyanion is a polyphosphate. In another aspect, the polyanion is a polymer having at least one fragment having the formula II

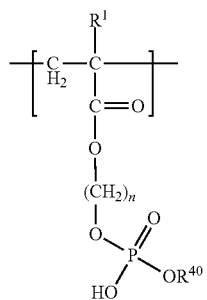

wherein $R^4$ is hydrogen or an alkyl group,
n is from 1 to 10,
$R^{40}$ is hydrogen, an alkyl group, or an aryl group, or

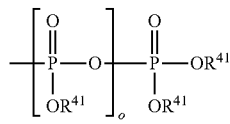

wherein $R^{41}$ is, independently, hydrogen, an alkyl group, an aryl group, a phosphate group, or the pharmaceutically-acceptable salt thereof.

Figure 6:
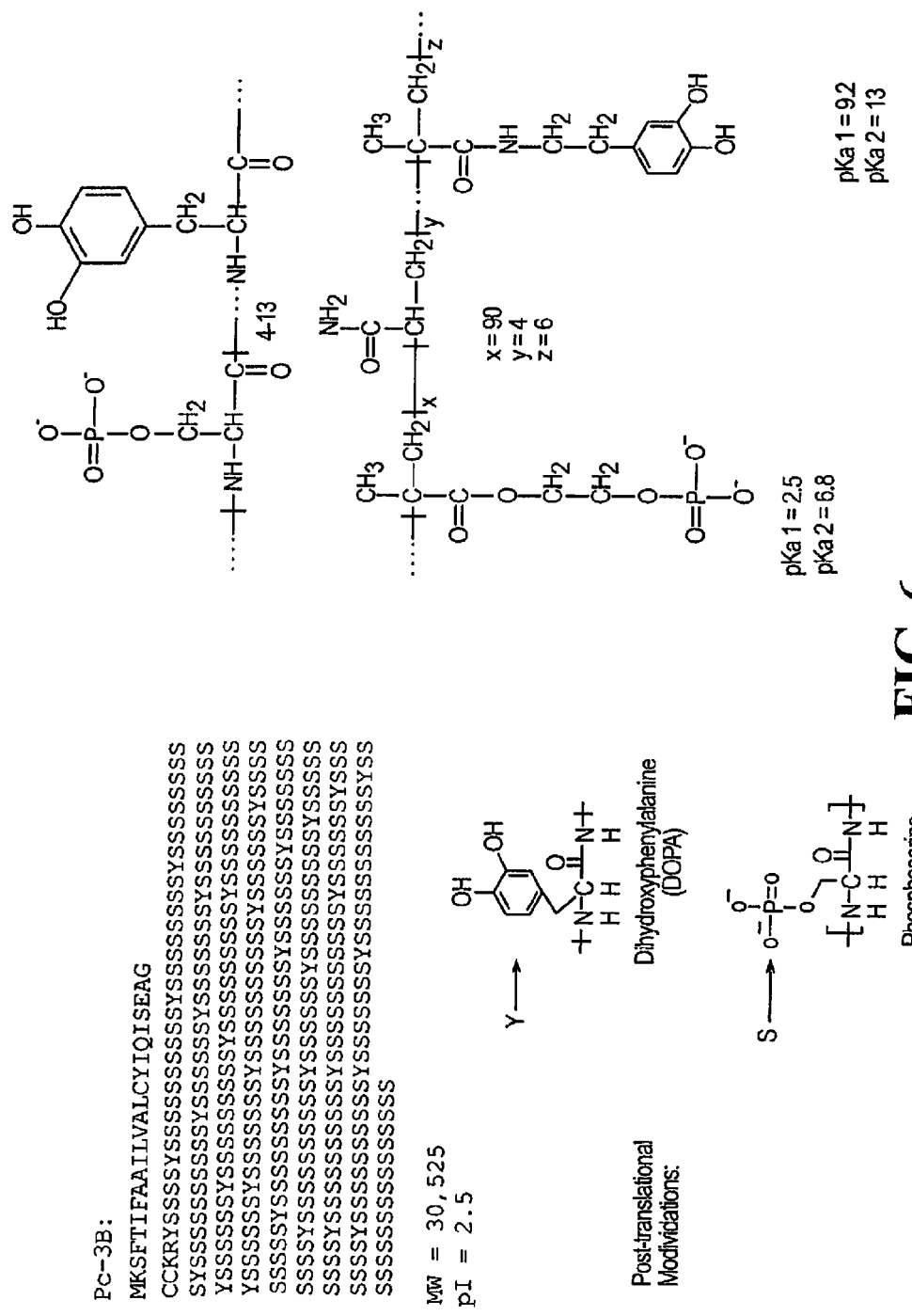

In another aspect, wherein $R^4$ is methyl, $R^{40}$ is hydrogen, and n is 2. Similar to formula I, the polymer backbone of formula II is composed of a residue of an acrylate or methacrylate. The remaining portion of formula II is the pendant phosphate group. FIG. 6 (structure B), shows an example of a polyanion useful herein that has the fragment of formula II, where the polymer backbone is derived from acrylamide and methacrylate residues. In one aspect, the polyanion is the copolymerization product of ethylene glycol methacrylate phosphate and acrylamide, where the molecular weight is from 10,000 to 50,000, preferably 30,000, and has phosphate groups in the amount of 45 to 90 mol %.

In another aspect, the polycation or polyanion are electrostatically associated block copolymers. The electrostatically associated block copolymers are water-soluble polymers composed of a polymer backbone with alternating polycationic blocks (i.e., blocks having a net positive charge) and polyanionic blocks (i.e., blocks having a net negative charge). Individual positive or negative charged groups are present in each block. The groups can be pendant to the polymer backbone and/or incorporated within the polymer backbone. In certain aspects, (e.g., biomedical applications), the polycationic blocks are composed of a series of cationic groups or groups that can be readily converted to cationic groups by adjusting the pH. In one aspect, the polycationic block is a polyamine compound. The amino groups of the polyamine can be branched or part of the polymer backbone. The amino group can be a primary, secondary, tertiary, or a guanidinium group that can be protonated to produce a cationic ammonium group at a selected pH.

In one aspect, the polycationic block of the copolymer can be derived from residues of lysine, histidine, arginine, and/or imidazole. Any anionic counterions can be used in association with the polycationic block. The counterions should be physically and chemically compatible with the essential components of the composition and do not otherwise unduly impair product performance, stability or aesthetics. Non-limiting examples of such counterions include halides (e.g., chloride, fluoride, bromide, iodide), sulfate and methylsulfate.

In another aspect, the polycationic block can be a biodegradable polyamine. The biodegradable polyamine can be any of the synthetic polymers or naturally-occurring polymers described above. In one aspect, when the polycationic block is an amine-modified natural polymer, the amine-modified natural polymer can include an aryl group having one or more amino groups directly or indirectly attached to the aromatic group. Alternatively, the amino group can be incorporated in the aromatic ring. For example, the aromatic amino group is a pyrrole, an isopyrrole, a pyrazole, imidazole, a triazole, or an indole. In another aspect, the aromatic amino group includes the isoimidazole group present in histidine. In another aspect, the biodegradable polyamine can be gelatin modified with ethylenediamine.

In one aspect, the polycationic block includes a polyacrylate having one or more pendant amino groups. For example, the backbone of the polycationic block can be a homopolymer or copolymer derived from the polymerization of acrylate or methacrylate monomers.

In other aspects, the polycationic block can in itself be a co-polymer (i.e., random or block), where segments or portions of the co-polymer possess cationic groups depending upon the selection of the monomers used to produce the co-polymer. In this aspect, the number of positively charged groups present in the polycationic block can vary from a few percent up to 100 percent (e.g., between 10 and 50%). In this aspect, the polycationic block can be the polymerization product between a neutral monomer (i.e., no charged groups) and a monomer possessing a positively charged group, where the amount of each monomer will determine the overall positive charge of the polycationic block. Thus, it is possible to produce different polycationic blocks within the electrostatically associated block copolymer.

Equations 1-3 below depict different embodiments regarding the polyactionic block. In equation 1, the same polycationic block (A) is incorporated into the block copolymer. In equation 2, two different polycationic blocks (A and B) are present in each polycationic block. In the case of the polycationic block AB in equation 2, monomers possessing different cationic groups can be used to produce the polycationic block AB. Thus, the polycationic block can in itself be a block copolymer. This is depicted in equation 2, where A depicts the first block in the polyactionic block and B depicts the second block. In equation 3, there are two different polycationic blocks, where each block (A and B) is the polymerization product of the same monomer.

$$\sim\!\!\sim A\!\sim\!\!\sim A\!\sim\!\!\sim A\!\sim\!\!\sim \qquad (1)$$

$$\sim\!\!\sim AB\!\sim\!\!\sim AB\!\sim\!\!\sim AB\!\sim\!\!\sim \qquad (2)$$

$$\sim\!\!\sim A\!\sim\!\!\sim B\!\sim\!\!\sim A\!\sim\!\!\sim \qquad (3)$$

In one aspect, the polycationic block has at least one fragment of the formula I described above.

Similar to the polycationic block, the polyanionic block in the copolymers described herein can be any synthetic polymer described above. The polyanionic block can in itself be a co-polymer (i.e., random or block), where segments or portions of the co-polymer possess cationic groups depending upon the selection of the monomers used to produce the co-polymer. In this aspect, the number of negatively charged groups present in the polyanionic block can vary from a few percent up to 100 percent (e.g., between 10 and 50%). In this aspect, the polyanionic block can be the polymerization product between a neutral monomer (i.e., no charged groups) and a monomer possessing a negatively charged group, where the amount of each monomer will determine the overall negative charge of the polyanionic block. Thus, it is possible to produce different polyanionic blocks within the electrostatically associated block copolymer.

In one aspect, the polyanionic block is a polyphosphate. In another aspect, the polyanion is a polyphosphate compound having from 10 to 90 mole % phosphate groups (i.e., a random co-polymer). For example, the polyphosphate can be a polymer with pendant phosphate groups attached to the polymer backbone of the polyanionic block and/or present in the polymer backbone of the polyanionic block (e.g., a phosphodiester backbone). In one aspect, the polyphosphate can be produced by chemically or enzymatically phosphorylating a protein (e.g., natural serine-rich proteins).

In one aspect, the polyanionic block includes a polyacrylate having one or more pendant phosphate groups. For example, the backbone of the polyanionic block can be a homopolymer or copolymer derived from the polymerization of acrylate monomers including, but not limited to, acrylates and methacrylates, Similar to above for the polycationic blocks as shown in equations 1-3, the polycationic blocks can be composed of the same or different blocks (A and B).

In one aspect, the polyanionic block is a polyphosphate. In another aspect, the polyanionic block is a polymer having at least one fragment having the formula X or II described above.

The polycations and polyanions useful herein have at least one crosslinking group. The mode of crosslinking between the polyelectrolyte can vary depending upon the nature of the crosslinking group. In one aspect, the crosslinking group can crosslink with itself without the need for additional reagents or chemistry. For example, a polycation that contains free thiol groups can crosslink with itself to produce disulfide bonds. Alternatively, a first polycation can have a nucleophilic group as a crosslinking group and a second polyelectrolyte can have an electrophilic group capable of reacting with the nucleophilic group. Examples of nucleophilic groups that are useful include, but are not limited to, hydroxyl, thiol, and nitrogen containing groups such as substituted or unsubstituted amino groups and imidazole groups. For example, residues of lysine, histidine, and/or cysteine or chemical analogs can be incorporated into the polycationic block and introduce nucleophilic groups. Examples of electrophilic groups include, but are not limited to, anhydride groups, esters, ketones, lactams (e.g., maleimides and succinimides), lactones, epoxide groups, isocyanate groups, and aldehydes. For example, a thiol group (nucleophile) on a first polyeletrolyte can react with an olefinic group (electrophile) on a second polyeletrolyte via a Michael addition to crosslink the two polyelectrolytes.

In other aspects, the crosslinking group present on the polyeletrolyte can undergo crosslinking via catalytic reactions. For example, the polyelectrolytes can possess alkynes and azides capable of undergoing cyclization via a Click reaction. Alternatively, crosslinking between the polyelectrolytes can be performed enzymatically (e.g. transglutaminase).

In one aspect, the crosslinking group is an actinically crosslinkable group. As used herein, "actinically crosslinkable group" in reference to curing or polymerizing means that the crosslinking of the polyelectrolyte is performed by actinic irradiation, such as, for example, UV irradiation, visible light irradiation, ionized radiation (e.g. gamma ray or X-ray irradiation), microwave irradiation, and the like. Actinic curing methods are well-known to a person skilled in the art. The actinically crosslinkable group can be an unsaturated organic group such as, for example, an olefinic group. Examples of olefinic groups useful herein include, but are not limited to, an acrylate group, a methacrylate group, an acrylamide group, a methacrylamide group, an allyl group, a vinyl group, a vinylester group, or a styrenyl group. In certain aspects, when the crosslinking group is an actinically crosslinkable group, the polyelectrolyte is capable of crosslinking with it self in the presence of an initiator. Alternatively, the actinically crosslinkable groups can polymerize with any of the polymerizable monomers described herein.

In another aspect, the crosslinking group includes a dihydroxyl-substituted aromatic group capable of undergoing oxidation in the presence of an oxidant. In one aspect, the dihydroxyl-substituted aromatic group is a dihydroxyphenol or halogenated dihydroxyphenol group such as, for example, DOPA and catechol (3,4 dihydroxyphenol). For example, in the case of DOPA, it can be oxidized to dopaquinone. Dopaquinone is an electrophilic group that is capable of either reacting with a neighboring DOPA group or another nucleophilic group. In the presence of an oxidant such as oxygen or other additives including, but not limited to, peroxides, periodates (e.g., $NaIO_4$), persulfates, permanganates, dichromates, transition metal oxidants (e.g., a $Fe^{+3}$ compound, osmium tetroxide), or enzymes (e.g., catechol oxidase), the dihydroxyl-substituted aromatic group can be oxidized. In another aspect, crosslinking can occur between the polycation and polyanion via light activated crosslinking through azido groups. Once again, new covalent bonds are formed during this type of crosslinking.

In certain aspects, the oxidant can be stabilized. For example, a compound that forms a coordination complex with periodate that is not redox active can result in a stabilized oxidant. In other words, the periodate is stabilized in a non-oxidative form and cannot oxidize the dihydroxyl-substituted aromatic group while in the complex. The coordination complex is reversible and even if it has a very high stability constant there is a small amount of uncomplexed periodate present. The dihydroxyl-substituted aromatic group competes with the compound for the small amount of free periodate. As the free periodate is oxidized more is released from the reversible complex. In one aspect, sugars possessing a cis,cis-1,2,3-triol grouping on a six-membered ring can form competitive periodate complexes. An example of a specific compound that forms stable periodate complex is 1,2-O-isopropylidene-alpha-D-glucofuranose. The stabilized oxidant can control the rate of crosslinking. Not wishing to be bound by theory, the stabilized oxidant slows down the rate of oxidation so that there is time to add the oxidant and position the substrate before the fiber (i.e., adhesive) hardens irreversibly.

The stability of the oxidized crosslinker can vary. For example, polyanions described herein can contain oxidizable crosslinkers that are stable in solution and do not crosslink with each other. This permits nucleophilic groups present on another polyanion to react with the oxidized crosslinker. This is a desirable feature, which permits the formation of intermolecular bonds and, ultimately, the formation of a strong adhesive.

Not wishing to be bound by theory, the polyelectrolyte with the dihydroxyl aromatic group(s) are stable in that they react slowly with itself in solution. Thus, the polyeletrolyte reacts with itself primarily via intermolecular cross-linking (e.g., polycation has a nucleophilic group or a dihydroxyl aromatic group) to produce a simple adhesive coacervate. This provides numerous advantages with respect to the use and administration of the adhesive. For example, the polyelectrolyte can be premixed and administered to a subject instead of the sequential administration of the polymers. This greatly simplifies administration of the coacervate and ultimately the adhesive that is not an option with currently available bioadhesives.

In other aspects, the crosslinking group present on the polyeletrolyte can form coordination complexes with transition metal ions. For example, a transition metal ion can be added to a mixture of polyeletrolyte, where the polyeletrolyte contains crosslinking groups capable of coordinating with the transition metal ion. The rate of coordination and dissociation can be controlled by the selection of the crosslinking group, the transition metal ion, and the pH. Thus, in addition to covalent crosslinking as described above, crosslinking can occur through electrostatic, ionic, or other non-covalent bonding. Transition metal ions such as, for example, iron, copper, vanadium, zinc, and nickel can be used herein.

In order to produce the simple adhesive coacervate, a sufficient amount a complimentary counterion is used. The nature and amount of complimentary counterion that is used will vary depending upon, among other things, the polyeletrolyte that is selected, the pH used to make the coacervate, and the dielectric constant of the solution used to prepare the coacervate. Methods for producing the simple adhesive coacervate are described in detail below.

In certain aspects, when the polyeletrolyte is a polyanion, the complimentary counterion is a multivalent cation (i.e., cations having a charge of +2 or greater). In one aspect, the multivalent cation can be a divalent cation composed of one or more alkaline earth metals. For example, the divalent cation can be $Ca^{+2}$ and/or $Mg^{+2}$. In other aspects, transition metal ions with a charge of +2 or greater can be used as the multivalent cation. In other aspects, when the polyeletrolyte is a polycation, the complimentary counterion can be a sulfate, a sulfonate, a carboxylate, a borate, a boronate, a substituted or unsubstituted phosphate, or a phosphonate.

In certain aspects, prior to crosslinking the simple adhesive coacervate, the coacervate can include one or more polymerizable monomers capable of undergoing polymerization in order to produce an internal network within the coacervate. The selection of the polymerizable monomer can vary depending upon the application. Factors such as molecular weight can be altered in order to modify the solubility properties of the polymerizable monomer in water.

The selection of the functional group on the polymerizable monomer determines the mode of polymerization. For example, the polymerizable monomer can be a polymerizable olefinic monomer that can undergo polymerization through mechanisms such as, for example, free radical polymerization and Michael addition reactions. In one aspect, the polymerizable monomer has two or more olefinic groups. In one aspect, the monomer comprises one or two actinically crosslinkable groups as defined herein in the presence of a photoinitiator. Alternatively, polymerization can be performed in the presence of thermal or chemical initiators, which are also discussed in detail below.

Examples of hydrophilic polymerizable monomers include, but not limited to, hydroxyalkyl methacrylate (HEMA), hydroxyalkyl acrylate, N-vinyl pyrrolidone, N-methyl-3-methylidene-pyrrolidone, allyl alcohol, N-vinyl alkylamide, N-vinyl-N-alkylamide, acrylamides, methacrylamide, (lower alkyl)acrylamides and methacrylamides, and hydroxyl-substituted (lower alkyl)acrylamides and -methacrylamides. In one aspect, the polymerizable monomer is a diacrylate compound or dimethacrylate compound. In another aspect, the polymerizable monomer is a polyalkylene oxide glycol diacrylate or dimethacrylate. For example, the polyalkylene can be a polymer of ethylene glycol, propylene glycol, or block co-polymers thereof. In one aspect, the polymerizable monomer is polyethylene glycol diacrylate or polyethylene glycol dimethacrylate. In one aspect, the polyethylene glycol diacrylate or polyethylene glycol dimethacrylate has a $M_n$ of 200 to 2,000, 400 to 1,500, 500 to 1,000, 500 to 750, or 500 to 600.

In other aspects, the simple adhesive coacervate can include a water-insoluble filler. Not wishing to be bound by theory, stress transfer from the polymeric matrix to the rigid filler can be reasonably expected to provide greater strength and a higher elastic modulus to the coacervate. The filler can have a variety of different sizes and shapes, ranging from particles to fibrous materials. In one aspect, the filler is a nano-sized particle. Compared to micron-sized silica fillers, nanoscale fillers have several desirable properties. First, with regard to toughening properties, nano-particles have been shown to be more effective in some cases than micro-particles. The higher specific surface area of nano- vs. microparticles increases the stress transfer from the polymer matrix to the rigid filler. Second, smaller volumes of nanofiller are required than of the larger micron-sized particles for a greater increase in toughness.

Additionally, an important consequence of the smaller diameters and lower fill volumes of nanoparticles is reduced viscosity of the uncured adhesive, which has direct benefits for processability. This is advantageous, as the coacervate can retain its injectable character while potentially increasing bond strengths dramatically. Third, maximum toughening requires uniform dispersion of the filler particles within the adhesive. Nanoscale colloidal particles, again because of the small diameter, lend themselves more readily to stable dispersions within the coacervate. In the case of state-of-the-art filled epoxy adhesives, gel-sol techniques create nearly perfect dispersions of nanosilica.

In one aspect, the filler comprises a metal oxide, a ceramic particle, or a water insoluble inorganic salt. Examples of the nanoparticles or nanopowders useful herein include those manufactured by SkySpring Nanomaterials, Inc., which are listed below.

Metals and Non-metal Elements
Ag, 99.95%, 100 nm
Ag, 99.95%, 20-30 nm
Ag, 99.95%, 20-30 nm, PVP coated
Ag, 99.9%, 50-60 nm
Ag, 99.99%, 30-50 nm, oleic acid coated
Ag, 99.99%, 15 nm, 10 wt %, self-dispersible
Ag, 99.99%, 15 nm, 25 wt %, self-dispersible
Al, 99.9%, 18 nm
Al, 99.9%, 40-60 nm
Al, 99.9%, 60-80 nm
Al, 99.9%, 40-60 nm, low oxygen
Au, 99.9%, 100 nm
Au, 99.99%, 15 nm, 10 wt %, self-dispersible
B, 99.9999%
B, 99.999%

B, 99.99%
B, 99.9%
B, 99.9%, 80 nm
Diamond, 95%, 3-4 nm
Diamond, 93%, 3-4 nm
Diamond, 55-75%, 4-15 nm
Graphite, 93%, 3-4 nm
Super Activated Carbon, 100 nm
Co, 99.8%, 25-30 nm
Cr, 99.9%, 60-80 nm
Cu, 99.5%, 300 nm
Cu, 99.5%, 500 nm
Cu, 99.9%, 25 nm
Cu, 99.9%, 40-60 nm
Cu, 99.9%, 60-80 nm
Cu, 5-7 nm, dispersion, oil soluble
Fe, 99.9%, 20 nm
Fe, 99.9%, 40-60 nm
Fe, 99.9%, 60-80 nm
Carbonyl-Fe, micro-sized
Mo, 99.9%, 60-80 nm
Mo, 99.9%, 0.5-0.8 μm
Ni, 99.9%, 500 nm (adjustable)
Ni, 99.9%, 20 nm
Ni coated with carbon, 99.9%, 20 nm
Ni, 99.9%, 40-60 nm
Ni, 99.9%, 60-80 nm
Carbonyl-Ni, 2-3 μm
Carbonyl-Ni, 4-7 μm
Carbonyl-Ni—Al (Ni Shell, Al Core)
Carbonyl-Ni—Fe Alloy
Pt, 99.95%, 5 nm, 10 wt %, self-dispersible
Si, Cubic, 99%, 50 nm
Si, Polycrystalline, 99.99995%, lumps
Sn, 99.9%, <100 nm
Ta, 99.9%, 60-80 nm
Ti, 99.9%, 40-60 nm
Ti, 99.9%, 60-80 nm
W, 99.9%, 40-60 nm
W, 99.9%, 80-100 nm
Zn, 99.9%, 40-60 nm
Zn, 99.9%, 80-100 nm
Metal Oxides
AlOOH, 10-20 nm, 99.99%
$Al_2O_3$ alpha, 98+%, 40 nm
$Al_2O_3$ alpha, 99.999%, 0.5-10 μm
$Al_2O_3$ alpha, 99.99%, 50 nm
$Al_2O_3$ alpha, 99.99%, 0.3-0.8 μm
$Al_2O_3$ alpha, 99.99%, 0.8-1.5 μm
$Al_2O_3$ alpha, 99.99%, 1.5-3.5 μm
$Al_2O_3$ alpha, 99.99%, 3.5-15 μm
$Al_2O_3$ gamma, 99.9%, 5 nm
$Al_2O_3$ gamma, 99.99%, 20 nm
$Al_2O_3$ gamma, 99.99%, 0.4-1.5 μm
$Al_2O_3$ gamma, 99.99%, 3-10 μm
$Al_2O_3$ gamma, Extrudate
$Al_2O_3$ gamma, Extrudate
$Al(OH)_3$, 99.99%, 30-100 nm
$Al(OH)_3$, 99.99%, 2-10 μm
Aluminium Iso-Propoxide (AIP), $C_9H_{21}O_3Al$, 99.9%
AlN, 99%, 40 nm
BaTiO3, 99.9%, 100 nm
$BBr_3$, 99.9%
$B_2O_3$, 99.5%, 80 nm
BN, 99.99%, 3-4 μm
BN, 99.9%, 3-4 nm
$B_4C$, 99%, 50 nm
$Bi_2O_3$, 99.9%, <200 nm
$CaCO_3$, 97.5%, 15-40 nm
$CaCO_3$, 15-40 nm
$Ca_3(PO_4)_2$, 20-40 nm
$Ca_{10}(PO_4)_6(OH)_2$, 98.5%, 40 nm
$CeO_2$, 99.9%, 10-30 nm
CoO, <100 nm
$CO_2O_3$, <100 nm
$CO_3O_4$, 50 nm
CuO, 99+%, 40 nm
$Er_2O_3$, 99.9%, 40-50 nm
$Fe_2O_3$ alpha, 99%, 20-40 nm
$Fe_2O_3$ gamma, 99%, 20-40 nm
$Fe_3O_4$, 98+%, 20-30 nm
$Fe_3O_4$, 98+%, 10-20 nm
$Gd_2O_3$, 99.9%<100 nm
$HfO_2$, 99.9%, 100 nm
$In_2O_3:SnO_2$=90:10, 20-70 nm
$In_2O_3$, 99.99%, 20-70 nm
$In(OH)_3$, 99.99%, 20-70 nm
$LaB_6$, 99.0%, 50-80 nm
$La_2O_3$, 99.99%, 100 nm
$LiFePO_4$, 40 nm
MgO, 99.9%, 10-30 nm
MgO, 99%, 20 nm
MgO, 99.9%, 10-30 nm
$Mg(OH)_2$, 99.8%, 50 nm
$Mn_2O_3$, 98+%, 40-60 nm
$MoCl_5$, 99.0%
$Nd_2O_3$, 99.9%, <100 nm
NiO, <100 nm
$Ni_2O_3$, <100 nm
$Sb_2O_3$, 99.9%, 150 nm
$SiO_2$, 99.9%, 20-60 nm
$SiO_2$, 99%, 10-30 nm, treated with Silane Coupling Agents
$SiO_2$, 99%, 10-30 nm, treated with Hexamethyldisilazane
$SiO_2$, 99%, 10-30 nm, treated with Titanium Ester
$SiO_2$, 99%, 10-30 nm, treated with Silanes
$SiO_2$, 10-20 nm, modified with amino group, dispersible
$SiO_2$, 10-20 nm, modified with epoxy group, dispersible
$SiO_2$, 10-20 nm, modified with double bond, dispersible
$SiO_2$, 10-20 nm, surface modified with double layer, dispersible
$SiO_2$, 10-20 nm, surface modified, super-hydrophobic & oleophilic, dispersible
$SiO_2$, 99.8%, 5-15 nm, surface modified, hydrophobic & oleophilic, dispersible
$SiO_2$, 99.8%, 10-25 nm, surface modified, super-hydrophobic, dispersible
SiC, beta, 99%, 40 nm
SiC, beta, whisker, 99.9%
$Si_3N_4$, amorphous, 99%, 20 nm
$Si_3N_4$ alpha, 97.5-99%, fiber, 100 nm×800 nm
$SnO_2$, 99.9%, 50-70 nm
ATO, $SnO_2:Sb_2O_3$=90:10, 40 nm
$TiO_2$ anatase, 99.5%, 5-10 nm
$TiO_2$ Rutile, 99.5%, 10-30 nm
$TiO_2$ Rutile, 99%, 20-40 nm, coated with $SiO_2$, highly hydrophobic
$TiO_2$ Rutile, 99%, 20-40 nm, coated with $SiO_2/Al_2O_3$
$TiO_2$ Rutile, 99%, 20-40 nm, coated with $Al_2O_3$, hydrophilic
$TiO_2$ Rutile, 99%, 20-40 nm, coated with $SiO_2/Al_2O_3$/Stearic Acid
$TiO_2$ Rutile, 99%, 20-40 nm, coated with Silicone Oil, hydrophobic
TiC, 99%, 40 nm
TiN, 97+%, 20 nm $WO_3$, 99.5%, <100 nm
$WS_2$, 99.9%, 0.8 μm
$WCl_6$, 99.0%
$Y_2O_3$, 99.995%, 30-50 nm
ZnO, 99.8%, 10-30 nm
ZnO, 99%, 10-30 nm, treated with silane coupling agents
ZnO, 99%, 10-30 nm, treated with stearic acid
ZnO, 99%, 10-30 nm, treated with silicone oil
ZnO, 99.8%, 200 nm
$ZrO_2$, 99.9%, 100 nm
$ZrO_2$, 99.9%, 20-30 nm
$ZrO_2$-3Y, 99.9%, 0.3-0.5 um
$ZrO_2$-3Y, 25 nm
$ZrO_2$-5Y, 20-30 nm
$ZrO_2$-8Y, 99.9%, 0.3-0.5 μm
$ZrO_2$-8Y, 20 nm
ZrC, 97+%, 60 nm In one aspect, the filler is nanosilica. Nanosilica is commercially available from multiple sources in a broad size range. For example, aqueous Nexsil colloidal silica is available in diameters from 6-85 nm from Nyacol Nanotechnologies, Inc. Amino-modified nanosilica is also commercially available, from Sigma Aldrich for example, but in a narrower range of diameters than unmodified silica. Nanosilica does not contribute to the opacity of the adhesive, which is an important attribute of the coacervates and glues produced therefrom.

In another aspect, the filler can be composed of calcium phosphate. In one aspect, the filler can be hydroxyapatite, which has the formula $Ca_5(PO_4)_3OH$. In another aspect, the filler can be a substituted hydroxyapatite. A substituted hydroxyapatite is hydroxyapatite with one or more atoms substituted with another atom. The substituted hydroxyapatite is depicted by the formula $M_5X_3Y$, where M is Ca, Mg, Na; X is $PO_4$ or $CO_3$; and Y is OH, F, Cl, or $CO_3$. Minor impurities in the hydroxyapatite structure may also be present from the following ions: Zn, Sr, Al, Pb, Ba. In another aspect, the calcium phosphate comprises a calcium orthophosphate. Examples of calcium orthophosphates include, but are not limited to, monocalcium phosphate anhydrate, monocalcium phosphate monohydrate, dicalcium phosphate dihydrate, dicalcium phosphate anhydrous, octacalcium phosphate, beta tricalcium phosphate, alpha tricalcium phosphate, super alpha tricalcium phosphate, tetracalcium phosphate, amorphous tricalcium phosphate, or any combination thereof. In certain aspects, the calcium phosphate crystals include crystals possessing carbonate groups ($CO_3$), which can facilitate the adhesion of the coacervate to certain types of cells such as, for example, bone cells. In other aspects, the calcium phosphate can also include calcium-deficient hydroxyapatite, which can preferentially adsorb bone matrix proteins.

In certain aspects, the coacervate also includes one or more initiators. For example, a photoinitiator can be entrapped in the coacervate. Thus, when the photoinitiator is activated (e.g., exposed to light), polymerization of the polymerizable monomer also entrapped in the coacervate occurs to produce the internal network. Examples of photoinitiators include, but are not limited to a phosphine oxide, a peroxide group, an azide group, an α-hydroxyketone, or an α-aminoketone. In one aspect, the photoinitiator includes, but is not limited to, camphorquinone, benzoin methyl ether, 1-hydroxycyclohexylphenyl ketone, or Darocure® or Irgacure® types, for example Darocure® 1173 or Irgacure® 2959. The photoinitiators disclosed in European Patent No. 0632329, which are incorporated by reference, can be used herein. In other aspects, the photoinitiator is a water-soluble photoinitiator including, but not limited to, riboflavin, eosin, eosin y, and rose Bengal.

In certain aspects, multiple initiators can be used to broaden the absorption profile of the initiator system in order to increase the initiation rate. For example, two different photoinitiators can be employed that are activated by different wavelengths of light. In another aspect, a chemical initiator can be used in combination with a photoinitiator. In another aspect, a co-initiator can be used in combination with any of the polymerization initiators described herein. In one aspect, the co-initiator is 2-(diethylamino)ethyl acrylate, 2-(dimethylamino)ethyl acrylate, 2-(dimethylamino)ethyl benzoate, 2-(dimethylamino)ethyl methacrylate, 2-ethylhexyl 4-(dimethylamino)benzoate, 3-(dimethylamino)propyl acrylate, 4,4'-bis(diethylamino)benzophenone, or 4-(diethylamino)benzophenone.

In certain aspects, the photoinitiator and/or co-initiator are covalently attached to the polyelectrolyte. For example, the photoinitiator and/or co-initiator can be copolymerized with monomers used to make the polyelectrolyte. In one aspect, the photoinitiators and co-initiators can possess polymerizable olefinic groups such as acrylate and methacrylate groups (e.g., see examples of co-initiators above) that can be copolymerized with monomers described used to make the polycation and polyanion. In another aspect, the initiators can be chemically grafted onto the backbone of the polyelectrolyte. Thus, in these aspects, the photoinitiator and/or co-initiator are covalently attached to the polymer and pendant to the polymer backbone. This approach will simplify formulation and possibly enhance storage and stability.

The simple adhesive coacervate can be synthesized a number of different ways. In one aspect, coacervate is produced by preparing a solution comprising (1) a polyelectrolyte, wherein the polyelectrolyte comprises a polyanion or polycation but not a combination thereof, the polyeletrolyte comprises at least one crosslinking group, and (2) a sufficient amount of a complimentary counterion to produce a simple adhesive coacervate. As discussed above, the nature and amount of complimentary counterion used to coacervate can vary depending upon. In general, the amount of complimentary counterion is sufficient to produce a solution having a net overall charge approaching zero. It is when the net charge is neutral the simple adhesive coacervate is formed. The pH of the solution can change the charge density on the polyeletrolyte, which in turn changes the amount of complimentary counterion needed to make the coacervate. Additionally, the dielectric constant of the solution can also be modified to produce the coacervate. For example, organic solvents such as alcohols, aldehydes, esters, and carboxylic acids can be used herein. In one aspect, ethanol can be used to make the coacervates described herein. In the case when the adhesives are to be used in biomedical applications, it is desirable that the organic solvent be biocompatible. Exemplary methods for producing the simple adhesive coacervates described herein are provided in the Examples.

After the simple adhesive coacervate, the coacervate is crosslinked in order to produce an adhesive. The mode of crosslinking will vary depending upon the nature of the crosslinking groups present on the polyeletrolyte. Exemplary methods for crosslinking simple adhesive coacervates described herein to produce adhesives are provided in the Examples. In certain aspects, the polyelectrolytes possess crosslinking groups that are capable of crosslinking with each. These groups were discussed in detail above and do not require the use of a crosslinker. For example, if the crosslinking group is a dihydroxyl-substituted aromatic group (e.g., DOPA) capable of undergoing oxidation in the presence of an oxidant to produce dopaquinone, the dopaquinone is an electrophilic group that is capable of reacting with a neighboring DOPA group in the absence of a crosslinker In other aspects, a crosslinker is used to crosslink the polyelectrolytes. In one aspect, the crosslinker comprises at least two nucleophilic groups. Examples of nucleophilic groups include, but are not limited to, a hydroxyl group, a thiol group, an amino group, or any combination thereof. This, the crosslinker can have tow or more different nucleophilic groups present on the molecule. In one aspect, the crosslinker includes an oligoamine, an oligopeptide, or a polythiol. In the case of the oligoamine, this is an amine compound possessing 2 to 10 substituted and/or unsubstituted amino groups. Examples of suitable amino groups include, but are not limited to, heterocyclic amines and aromatic amines (e.g., imidazole). An oligopeptide is a peptide possessing from 2 to 10 amino acid residues. In one aspect, the oligopeptide can include enzyme cleavage sequences or cell adhesion sequences. An oligothiol is a compound possessing from 2 to 10 thiol groups.

In one aspect, the crosslinker comprises $H_2NCH_2NH_2$, $H_2NCH_2CH_2NH_2$, $H_2NCH_2CH_2CH_2NH_2$, $H_2NCH_2CH_2CH_2CH_2NH_2$, $H_2NCH_2CH_2CH_2CH_2CH_2NH_2$, $H_2NCH_2NHCH_2CH_2CH_2NH_2$, $H_2NCH_2CH_2NHCH_2CH_2CH_2NH_2$, $H_2NCH_2CH_2CH_2NHCH_2CH_2CH_2CH_2NHCH_2CH_2CH_2NH_2$, $H_2NCH_2CH_2NHCH_2CH_2CH_2CH_2NH_2$, or $H_2NCH_2CH_2NHCH_2CH_2CH_2NHCH_2CH_2CH_2NH_2$.

In other aspects, the crosslinker comprises a surface-modified nanoparticle. In certain aspects, any of the fillers described above can be functionalized with one or more functional groups that are capable of capable of reacting with a crosslinkable group on the polyeletrolyte and, when applicable, the polymerizable olefinic monomer. In this aspect, the filler is covalently attaches to the polyelectrolyte in order to crosslink the polyelectrolyte. For example, the filler particle can be modified with surface amines or thiols (i.e., nucleophiles) that can react with react with electrophilic groups present on the polyelectrolyte as described above. In other aspects, the filler can be modified to produce charged groups such that the filler can form electrostatic bonds with the polyeletrolyte. For example, aminated silica can be added to a solution and the pH adjusted so that the amino groups are protonated and available for electrostatic bonding.

In certain aspects, the polyelectrolyte can be crosslinked using multiple reagents and steps. In one aspect, the crosslinking step is performed in the presence of an oxidant and a crosslinker. For example, if the crosslinking group is a dihydroxyl-substituted aromatic group (e.g., DOPA) capable of undergoing oxidation in the presence of an oxidant to produce dopaquinone, the dopaquinone is an electrophilic group that is capable of reacting with a crosslinker possessing two or more nucleophilic groups. In one aspect, the crosslinker is an oligoamine, where an amino group reacts with the dopaquinone to produce a new covalent bond. Exemplary procedures for this aspect are provided in the Examples.

In another aspect, the crosslinker comprises two or more actinically crosslinkable groups. Any of the actinically crosslinkable groups described herein can be used as the crosslinker. Thus, when the polyelectrolyte has one or more actinically crosslinkable groups, the polyelectrolytes can be crosslinked with one with a crosslinker having two or more actinically crosslinkable groups in the presence of an initiator. Examples of such crosslinkers include, but are not limited to, diacrylates, dimethacrylates, and the like. In one aspect, the crosslinker can be a polyalkylene oxide glycol diacrylate or dimethacrylate. For example, the polyalkylene can be a polymer of ethylene glycol, propylene glycol, or block co-polymers thereof. In one aspect, the polymerizable monomer is polyethylene glycol diacrylate or polyethylene glycol dimethacrylate. In one aspect, the polyethylene glycol diacrylate or polyethylene glycol dimethacrylate has a $M_n$ of 200 to 2,000, 400 to 1,500, 500 to 1,000, 500 to 750, or 500 to 600.

Additional reaction conditions can be varied in order to facilitate crosslinking and produce the adhesive. In one aspect, the pH of the coacervate can be raised. For example, when the coacervate is applied at a pH of 5 and subsequently exposed to seawater at pH 8.2, the coacervate crosslinks spontaneously to produce the adhesive. The polyelectrolytes described herein can be stored as dry powders for extended periods of time. This feature is very useful for preparing the coacervates and ultimately the adhesives when desired. Thus, described herein are kits for making the complex coacervates and adhesives described herein. In one aspect, the kit comprises (1) a polyelectrolyte, wherein the polyelectrolyte comprises a polyanion or polycation but not a combination thereof, wherein the polyeletrolyte comprises at least one crosslinking group; (2) a sufficient amount of a complimentary counterion to produce a simple adhesive coacervate; and (3) a crosslinker. In another aspect, the kit comprises (1) a simple adhesive coacervate comprising (a) a polyelectrolyte, wherein the polyelectrolyte comprises a polyanion or polycation but not a combination thereof, the polyeletrolyte comprises at least one crosslinking group, and (b) a sufficient amount of a complimentary counterion to produce a simple adhesive coacervate, and (2) a crosslinker. In this aspect, the simple adhesive coacervate is pre-made.

When stored as dried powders, water can be added to the polyelectrolyte and complimentary counterion to produce the coacervate. In one aspect, prior to lyophilizing the polyelectrolyte in order to produce a dry powder, the pH of the polyelectrolyte can be adjusted such that when they are admixed in water the desired pH is produced with the addition of acid or base. For example, excess base can be present in the polyelectrolyte powder which upon addition of water adjusts the pH accordingly. The kits can include additional components as needed such as, for example, an oxidant, a polymerizable monomer and/or water-insoluble filler, and a polymerization initiator and optionally a co-initiator.

The adhesives described herein have numerous applications, particularly where the adhesive is to be used in aqueous environments. For example, the simple adhesive coacervates have low initial viscosity, specific gravity greater than one, and being mostly water by weight, low interfacial tension in an aqueous environment, all of which contribute to their ability to adhere to a wet surface. The simple adhesive coacervates prior to crosslinking can be applied to variety of substrates. The substrates can be wet or dry. Additionally, in certain aspects, the surface of the substrate can be primed prior to application of the coacervate. For example, the substrate surface can be primed with a separate solution before adding the coacervate to increase interfacial adhesion. For example, the surface can be cleaned or etched. Alternatively, the surface of the substrate can be modified with groups that can crosslink with the polyelectrolyte. For example, nucleophilic groups can be introduced to the surface of the substrate that crosslink with the polyelectrolyte. Examples of substrates that the coacervates can be applied to include, but are not limited to, metal substrates, foils, fibers, a tapes, or cloth. In certain aquatic applications (fresh or salt water), the substrate can include coral, a marker, a beacon, an ordinance, or a material for producing an artificial reef. The adhesives described herein have particular relevance in restoring aquatic ecosystems such reefs. Here, natural materials (e.g., coral) and other synthetic materials (e.g., calcium carbonate rocks, dead coral, reef plugs, coral plugs, coral mounting pieces, etc.) can be adhered to existing reefs in order to promote the growth of the reef.

Depending upon the application to be used, the adhesive can be prepared a number of different ways on the substrate. For example, when a crosslinker is used to produce the adhesive, the coacervate can be applied to the substrate first followed by the addition of the crosslinker to the coacervate. Alternatively, the crosslinker can be applied to the substrate first followed by the application of the coacervate. In another embodiment, the coacervate and crosslinker can be applied to the substrate simultaneously through a dual syringe. Here, the crosslinker and coacervate react with one another to produce the adhesive when it is applied to the substrate.

The adhesives produced herein have numerous biological applications as well. In one aspect, the adhesives are useful in adhering implantable devices in a subject. For example, stents, pins, and screws can be adhered in a subject using the adhesives described herein.

In other aspects, the substrate can be bone. For example, the adhesives can be used to repair a number of different bone fractures and breaks. Examples of such breaks include a complete fracture, an incomplete fracture, a linear fracture, a transverse fracture, an oblique fracture, a compression fracture, a spiral fracture, a comminuted fracture, a compacted fracture, or an open fracture. In one aspect, the fracture is an intra-articular fracture or a craniofacial bone fracture. Fractures such as intra-articular fractures are bony injuries that extend into and fragment the cartilage surface. The adhesives may aid in the maintenance of the reduction of such fractures, allow less invasive surgery, reduce operating room time, reduce costs, and provide a better outcome by reducing the risk of post-traumatic arthritis.

In other aspects, the adhesives can be used to join small fragments of highly comminuted fractures. In this aspect, small pieces of fractured bone can be adhered to an existing bone. For example, the coacervate can be applied to the fractured bone and/or the existing bone. It is especially challenging to maintain reduction of the small fragments by drilling them with mechanical fixators. The smaller and greater number of fragments the greater the problem. In one aspect, the adhesive may be injected in small volumes to create spot welds in order to fix the fracture rather than filling the entire crack. The small biocompatible spot welds would minimize interference with healing of the surrounding tissue and would not necessarily have to be biodegradable. In this respect it would be similar to permanently implanted hardware.

In other aspects, the adhesives can be used to secure scaffolds to bone and other tissues such as, for example, cartilage, ligaments, tendons, soft tissues, organs, membranous tissues (e.g., vaginal, nasal, amniotic membrane) and synthetic derivatives of these materials. Using the adhesives and spot welding techniques, the adhesive complex coacervates and adhesives produced therefrom can be used to position biological scaffolds in a subject. The adhesive can be applied to the biological scaffold and/or the bone or tissue prior to securing the scaffold. Small adhesive tacks would not interfere with migration of cells or transport of small molecules into or out of the scaffold. In certain aspects, the scaffold can contain one or more drugs that facilitate growth or repair of the bone and tissue. In other aspects, the scaffold can include drugs that prevent infection such as, for example, antibiotics. For example, the scaffold can be coated with the drug or, in the alternative, the drug can be incorporated within the scaffold so that the drug elutes from the scaffold over time.

The adhesives have numerous dental applications. Using the spot weld techniques, the adhesive can be applied to specific points in the mouth (e.g., jaw, sections of a tooth). For example, the adhesives can be used in the treatment of recession defects, increasing gingival tissue height and width, increase the amount of attached gingival tissue at the gingival margin, and increase the zone of attached gingival tissue. In oral surgery they could be used to improve soft tissue outcomes and grow new bone in guided bone regeneration procedures. Additionally, the adhesives can facilitate wound healing of gums after a periodontal procedure and help prevent or reduce bleeding. As will be discussed below, the adhesives can be used to deliver bioactive agents. Thus, the adhesives can be used to deliver bioactive agents to the gums and roots of teeth. In other aspects, the adhesives can be used to secure dental implants to teeth (e.g., crowns, dentures). Alternatively, the adhesives can be used as a primer to prepare the dentin or enamel surface of a tooth to bond dental cements.

In other aspects, the adhesives can adhere a substrate to bone. Examples of substrates include metal substrates (e.g., plates, medical implants, etc.), fibers, foils, pieces of cloth, or any other materials that can be implanted within a subject. The coacervate can be applied to the substrate and/or bone prior to use. For example, implants made from titanium oxide, stainless steel, or other metals are commonly used to repair fractured bones. The adhesives can be applied to the metal substrate, the bone, or both prior to adhering the substrate to the bone. In certain aspects, the crosslinking group present on the polyelectrolyte can form a strong bond with titanium oxide. For example, it has been shown that DOPA can strongly bind to wet titanium oxide surfaces (Lee et al., PNAS 103:12999 (2006)). Thus, in addition to bonding bone fragments, the adhesives described herein can facilitate the bonding of metal substrates to bone, which can facilitate bone repair and recovery.

It is also contemplated that the adhesives can include one or more bioactive agents. The bioactive agents can be any drug that will facilitate bone growth and repair when the complex is applied to the bone. The rate of release can be controlled by the selection of the materials used to prepare the complex as well as the charge of the bioactive agent if the agent is a salt. In certain aspects, when the adhesive is converted to an insoluble solid by a change in temperature and/or pH, the adhesive can be administered to a subject and produce an insoluble solid in situ. Thus, in this aspect, the insoluble solid can perform as a localized controlled drug release depot. It may be possible to simultaneously fix tissue and bones as well as deliver bioactive agents to provide greater patient comfort, accelerate bone healing, and/or prevent infections. In other aspects, the adhesives can include contrast agents typically used in imaging procedures such as MRI. In this aspect, the position and amount of the adhesive in the subject can be detected and monitored over time. Contrast agents typically used in the art can be used herein.

The adhesives can be used in a variety of other surgical procedures. For example, the adhesives can be used to treat ocular wounds caused by trauma or by the surgical procedure itself. In one aspect, the adhesives can be used to repair a corneal or schleral laceration in a subject. In other aspects, the adhesives can be used to facilitate healing of ocular tissue damaged from a surgical procedure (e.g., glaucoma surgery or a corneal transplant). The methods disclosed in U.S. Published Application No. 2007/0196454, which are incorporated by reference, can be used to apply the coacervates described herein to different regions of the eye.

In other aspects, the adhesives can be used to inhibit blood flow in a blood vessel of a subject. In general, the adhesive is injected into the vessel in order to partially or completely block the vessel. This method has numerous applications including hemostasis or the creation of an artificial embolism to inhibit blood flow to a tumor or aneurysm.

The adhesives described herein can seal the junction between skin and an inserted medical device such as catheters, electrode leads, needles, cannulas, osseo-integrated prosthetics, and the like. In this aspect, the adhesives prevent infection at the entry site when the device is inserted in the subject. In other aspects, the adhesives can be applied to the entry site of the skin after the device has been removed in order to expedite wound healing and prevent further infection.

In another aspect, the adhesives described herein can be used to close or seal a puncture in an internal tissue or membrane. In certain medical applications, internal tissues or membranes are punctured, which subsequently have to be sealed in order to avoid additional complications. Alternatively, the adhesives described herein can be used to adhere a scaffold or patch to the tissue or membrane in order to prevent further damage and facilitate wound healing.

In one aspect, the coacervates described herein can modify one or more the properties of a substrate. For example, the coacervates prior to crosslinking can modify the wettability, charge, or anti-fouling properties corrosion resistance, anti-fouling, of the surface as well as promote specific interactions on the surface (e.g. biomolecule attachment, cell attachment, metal ion coordination, etc.).

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Preparation of Simple Adhesive Coacervate

The simple adhesive coacervates were prepared as follows. Using multiple independent variables, coacervation of the MOEP-DOPA copolymer was determined using a Design of Experiment (DOE) matrix with JMP 8 software. Each independent variable (pH of the solution, Mg:$PO_4$ ratio, ratio of ethanol to deionized water) was chosen and limits set to create a window where coacervation may occur. Variables outside of the upper and lower limits would cause MOEP-DOPA copolymer to either create a gel or remain in solution. A design of experiment (DOE) was generated with 16 runs, varying pH, Mg:$PO_4$ ratio, and EtOH:$H_2O$ ratio. The results where rated based on appearance using a scale of 1-3 (1-In solution, 2-appearance of coacervate, 3-Gel/Solid). The resulting data was input into the DOE matrix and modeled using the software. The resulting parameters, based on the highest desirability for each parameter, resulted in a pH of 6.8, Mg: $PO_4$ ratio of 0.45, and EtOH:$H_2O$ ratio of 0.20.

The runs for the DOE where conducted at 5% wt MOEP-DOPA copolymer in solution. Each run was done in a 1.7 mL Ependorf tube, using a total 500 μL of solution, at room temperature. MOEP-DOPA copolymer (5% wt) was weighed into an empty tube. Deionized water with and without 450 mM of NaCl (simulated ocean water) was added and the tube vortexed on high until MOEP-DOPA copolymer went into solution. The pH of the solution was adjusted using a 6M solution of NaOH. The volume of NaOH used factored into total volume. The appropriate volume of $MgCl_2$ in deionized $H_2O$ with and without 450 mM of NaCl was slowly added to the solution while stirring. To this, ethanol was slowly added while stirring. The final solution was vortexed, left on ice for 1 hr, and then left at room temperature. The coacervate appeared within 2 hrs. Each run was rated based on appearance.

Preparation of Adhesive

Testing was done to maximize the bond strength based on the proportions of $NaIO_4$ used compared to DOPA present and to determine the affect of a diamine on the strength. Bond strengths were tested with Al strips. The coacervate was applied to a wet strip, the appropriate cross-linking solution (ethylenediamine dihydrochloride) added and stirred on the strip, and then covered with another wet strip and clamped together. Samples where incubated for 24 hrs in deionized $H_2O$ with and without 450 mM of NaCl at 37° C. After 24 hrs, each Al strip was mounted on the Instron in deionized $H_2O$ with and without 450 mM of NaCl at 37° C. and bond strengths were determined.

Figure 8:
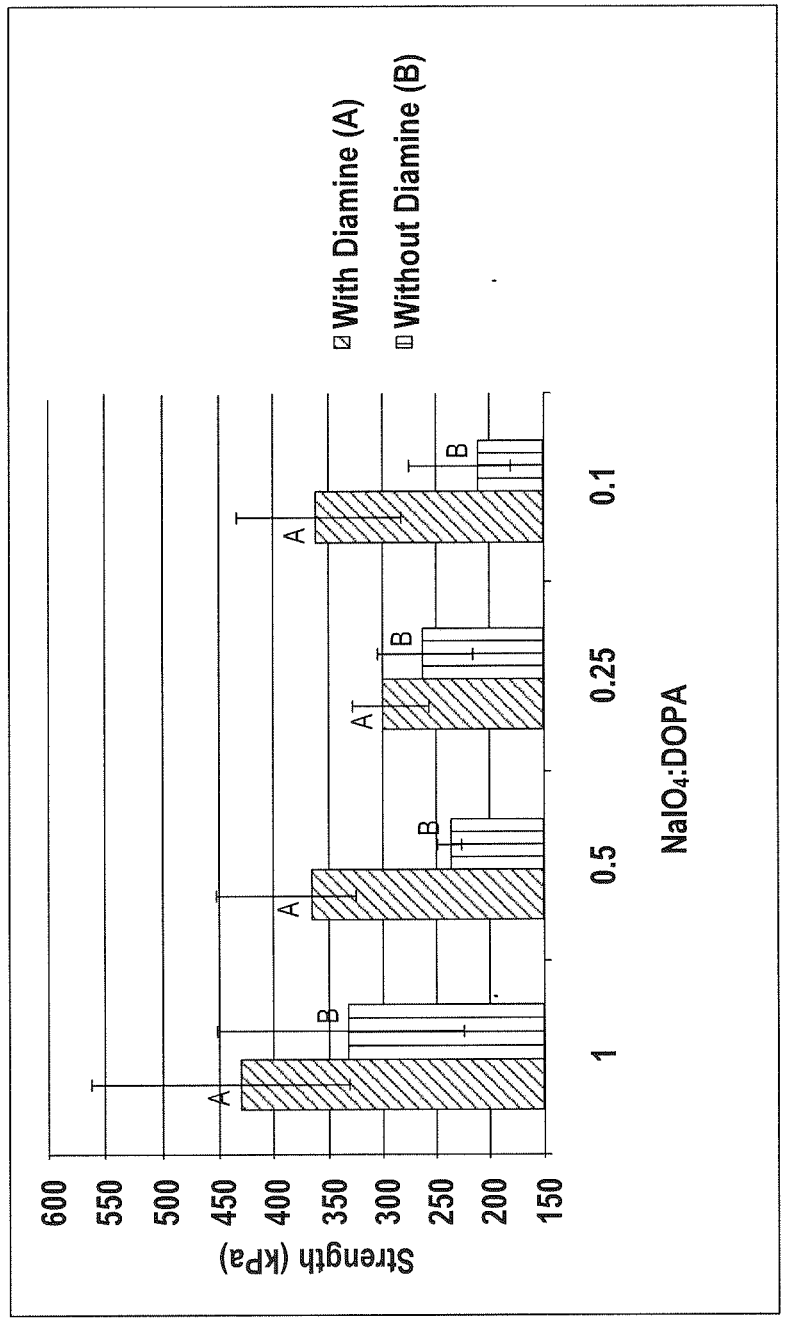
FIG. 8 shows a chart displaying the underwater bond strengths of adhesives prepared with polyphosphodopa on aluminum adherends in a standard lap shear configuration (450 kPa is roughly 60 psi).

The crosslinking solution was prepared using sodium m-periodate and 1, 2-O-isopropylidene-D-glucofuranose vortexed in deionized $H_2O$. The solution was prepared based on the $NaIO_4$:DOPA ratio. It was then applied to the coacervate on the strips. For samples requiring diamine, the $NaIO_4$/sugar solution was then added to ethylenediamine dihydrochloride and vortexed. The solution was then applied to the coacervate on the metal strips. FIG. 8 displays the underwater bond strengths of the adhesives on the aluminum adherends in a standard lap shear configuration (450 kPa is roughly 60 psi). Table 1 provides additional parameters for preparing numerous adhesives: (1) EtOH was 20% in experiments 1-13 and 30% in experiments 14-21; (2) Mg/PO4 was 0.45 in experiments 1-13 and 0.5 in experiments 14-21; (3) the amine was ethylenediamine; and (4) deionized water was used in experiments 1-14 and 16, and deionized water with 450 mM NaCl was used in experiments 16 and 18-21. Amine modified filler was added in experiments 12 and 13. In experiments 18 and 19, 5 mg of crushed coral was added.

Figure 9:
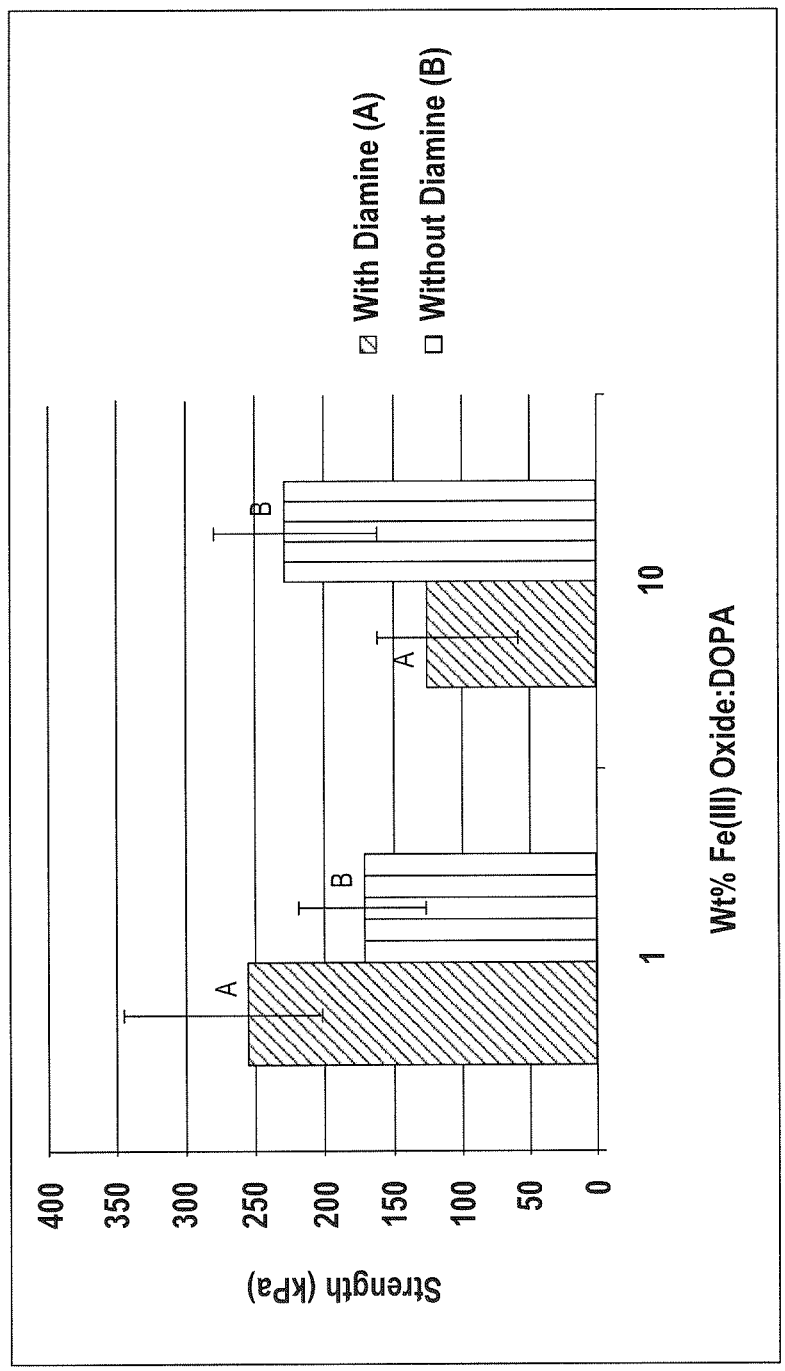
FIG. 9 shows a chart displaying the underwater bond strengths of adhesives prepared with polyphosphodopa on aluminum adherends in a standard lap shear configuration (450 kPa is roughly 60 psi), where iron (III) oxide nanoparticles are used as the oxidant and filler.

In Experiments 22-25 use Fe(III) oxide nanoparticles were used as the oxidant and filler, where wt % of Fe2O3:DOPA is in the coacervate. The samples were incubated and tested in instant ocean sea water (pH 8.4). The results are shown in Table 1 and FIG. 9.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

TABLE 1

| Ex. No. | Total DOPA | Coacervate DOPA | % DOPA in Coacervate | Strength (kPa) 1 | 2 | 3 | 4 | 5 | PhosphoDOPA (mg) | Amine (mg) | DOPA:NaIO4 | pH |
|---|---|---|---|---|---|---|---|---|---|---|---|---|
| 1 | 3.92E−05 | 2.98E−05 | 76.02 | 41 | 56 | 307 | | | 47.39 | 2.61 | 1:1 | 6.55 |
| 2 | 4.14E−05 | 2.98E−05 | 71.98 | 220 | | | | | 50 | | 1:1 | 6.48 |
|   | 3.92E−05 |          |       |     |     |     |     |     |       | 2.61 | 1:1 | 6.77 |
| 3 |          | 2.55E−05 | 65.05 | 563 | 488 | 330 | 343 | | 47.39 | | | |
| 4 | 3.92E−05 | 2.55E−05 | 65.05 | 369 | 112 | 202 | 102 | | 47.39 | 2.61 | 2:1 | 6.77 |
| 5 | 3.92E−05 | 1.32E−05 | 33.67 | 256 | 300 | 328 | 326 | | 47.39 | 2.61 | 4:1 | 6.8 |
| 6 | 3.92E−05 | 1.32E−05 | 33.67 | 317 | 432 | 420 | 281 | | 47.39 | 2.61 | 10:1 | 6.8 |
| 7 | 4.14E−05 | 1.20E−05 | 28.99 | 410 | 450 | 224 | 249 | | 50 | | 1:1 | 6.68 |
| 8 | 4.14E−05 | 1.20E−05 | 28.99 | 226 | 249 | | | | 50 | | 2:1 | 6.68 |
| 9 | 4.14E−05 | 1.33E−05 | 32.13 | 273 | 215 | 304 | | | 50 | | 4:1 | 6.73 |
| 10 | 4.14E−05 | 1.33E−05 | 32.13 | 274 | 193 | 196 | 180 | | 50 | | 10:1 | 6.73 |
| 11 | 4.14E−05 | 1.89E−05 | 45.65 | 18 | 68 | | | | 50 | | 1:1 | 6.48 |
| 12 | 3.34E−05 | 1.88E−05 | 56.29 | 20 | 78 | 143 | | | 38.19 | 11.81 | 1:1 | 6.81 |
| 13 | 3.34E−05 | 1.60E−05 | 47.90 | 55 | 105 | | | | 38.19 | 11.81 | 1:1 | 7.3 |
| 14 | 4.38E−05 | 1.51E−05 | 34.47 | 4 | 114 | 4 | 84 | | 50 | | | 5.11 |
| 15 | 4.38E−05 | 3.34E−05 | 76.26 | 15 | 169 | 257 | 333 | | 50 | | | 5.4 |
| 16 | 4.38E−05 | 1.51E−05 | 34.47 | 36 | 0.6 | 1.8 | 52 | | 50 | | 1:1 | 5.11 |
| 17 | 4.38E−05 | 3.34E−05 | 76.26 | 355 | 185 | 233 | | | 50 | | 1:1 | 5.4 |
| 18 | 4.38E−05 | 3.36E−05 | 76.71 | 93 | 27 | 98 | | | 50 | | | 5.47 |
| 19 | 4.38E−05 | 3.36E−05 | 76.71 | 137 | 270 | 120 | | | 50 | | 1:1 | 5.47 |
| 20 | 4.14E−05 | 3.25E−05 | 78.50 | 118 | 10 | 127 | 7.6 | | 47.25 | 2.75 | 1:1 | 5.73 |
| 21 | 4.14E−05 | 3.27E−05 | 78.99 | 9.5 | 229 | 91 | 142 | 135 | 47.25 | 2.75 | | 5.27 |
| 22 | 3.95E−05 | 3.30E−05 | 83.54 | 202.7 | 344 | 224 | | | 47.38 | 2.62 | 1% wt Fe$_2$O$_3$ | 6.16 |
| 23 | 4.16E−05 | 2.67E−05 | 64.18 | 4.23 | 0.75 | 219 | 126 | | 50 | | 1% wt Fe$_2$O$_3$ | 5.63 |
| 24 | 3.95E−05 | 3.30E−05 | 83.54 | 158 | 12.7 | 161 | 56.9 | | 47.38 | 2.62 | 10% wt Fe$_2$O$_3$ | 6.16 |
| 25 | 4.16E−05 | 2.67E−05 | 64.18 | 162 | 280 | 248 | | | 50 | | 10% wt Fe$_2$O$_3$ | 5.63 |

What is claimed:

1. An adhesive produced by the process comprising
   (a) preparing a simple adhesive coacervate comprising (1) a polyelectrolyte, wherein the polyelectrolyte comprises a polyanion or polycation but not a combination thereof, the polyeletrolyte comprises at least one crosslinking group, and wherein a photoinitiator and optionally a co-initiator are covalently attached to the polycation and/or polyanion, (2) a sufficient amount of a complimentary counterion to produce a simple adhesive coacervate, and (3) a polymerizable monomer, a water-insoluble filler, or a combination thereof; and
   (b) crosslinking the simple adhesive coacervate to produce the adhesive.

2. The adhesive of claim 1, wherein the polycation comprises electrostatically associated block copolymers, wherein the block co-polymers comprise alternating polycationic blocks and polyanionic blocks, and the polycation has a net positive charge at the pH the simple adhesive coacervate is formed.

3. The adhesive of claim 1, wherein the polycation comprises a polysaccharide, a protein, a synthetic polyamine, or a synthetic polypeptide.

4. The adhesive of claim 1, wherein the polycation comprises an amine-modified natural polymer.

5. The adhesive of claim 1, wherein the polyanion comprises electrostatically associated block copolymers, wherein the block co-polymers comprise alternating polycationic blocks and polyanionic blocks, and the polyanion has a net negative charge at the pH the simple adhesive coacervate is formed.

6. The adhesive of claim 1, wherein the polyanion comprises a polysaccharide, a protein, or a synthetic polypeptide.

7. The adhesive of claim 1, wherein the polyanion comprises one or more sulfate, sulfonate, carboxylate, borate, boronate, phosphonate, phosphate groups, or any combination thereof.

8. The adhesive of claim 1, wherein the polyeletrolyte comprises a polyanion and the complimentary counterion comprises at least one multivalent metal cation comprising one or more divalent cations, one or more transition metal ions, or rare earth metal ions.

9. The adhesive of claim 1, wherein the adhesive further comprises one or more bioactive agents.

10. A substrate comprising an adhesive of claim 1 on at least one surface of the substrate.

11. A method for modifying the one or more surface properties of a substrate, the method comprising applying to the substrate surface a simple adhesive coacervate prepared by combining (1) a polyelectrolyte, wherein the polyelectrolyte comprises a polyanion or polycation but not a combination thereof, the polyeletrolyte comprises at least one crosslinking group, and wherein a photoinitiator and optionally a co-initiator are covalently attached to the polycation and/or polyanion (2) a sufficient amount of a complimentary counterion to produce a simple adhesive coacervate, and (3) a polymerizable monomer, a water-insoluble filler, or a combination thereof, wherein a photoinitiator and optionally a co-initiator are covalently attached to the polycation and/or polyanion.

12. The adhesive of claim 3, wherein the protein comprises a recombinant protein.

13. The adhesive of claim 6, wherein the polysaccharide comprises a hyaluronate, arabic gum, an alginate, chondroitin sulfate, dermatan, dermatan sulfate, heparan sulfate, or any combination thereof.

14. The adhesive of claim 1, wherein the polyanion comprises a polyphosphate compound.

15. The adhesive of claim 1, wherein the polyanion comprises a polyacrylate comprising one or more pendant phosphate groups.

16. The adhesive of claim 1, wherein the polyanion comprises a polymer comprising at least one fragment comprising the formula X

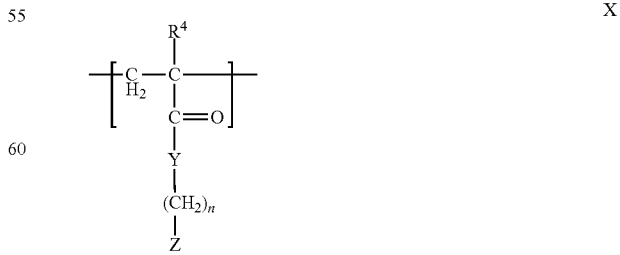

wherein $R^4$ is hydrogen or an alkyl group;
n is from 1 to 10;

Y is oxygen, sulfur, or $NR^{30}$, wherein $R^{30}$ is hydrogen, an alkyl group, or an aryl group;

Z is sulfate, sulfonate, carboxylate, borate, boronate, a substituted or unsubstituted phosphate, or a phosphonate, or the pharmaceutically-acceptable salt thereof.

17. The adhesive of claim 1, wherein the crosslinking group comprises an actinically crosslinkable group.

18. The adhesive of claim 1, wherein the monomer comprises two or more olefinic groups.

19. The adhesive of claim 1, wherein the filler comprises a metal oxide, a ceramic particle, or a water insoluble inorganic salt.

20. The adhesive of claim 1, wherein the filler comprises nanosilica, microsilica, hydroxyapatite or substituted hydroxyapatite, a nano calcium phosphate particle, alpha-tricalcium phosphate, beta-tricalcium phosphate, amorphous-tricalcium phosphate, or any combination thereof.

21. The adhesive of claim 1, wherein the water-insoluble filler comprises is functionalized with or more functional groups that react with a crosslinkable group on the polycation, the polyanion, or a combination thereof.

22. The adhesive of claim 1, wherein the polymerization initiator comprises (1) one or more of a free radical initiator, a thermal initiator, or a photoinitiator, or (2) two or more radical initiators, thermal initiators, or a photoinitiators.

23. The adhesive of claim 1, wherein the photoinitiator comprises a water-soluble initiator comprising riboflavin, eosin, eosin y, or rose Bengal.

24. The adhesive of claim 1, wherein the adhesive further comprises one or more contrast agents.

25. The adhesive of claim 1, wherein the crosslinking step (b) comprises exposing the simple adhesive coacervate to UV irradiation, visible light irradiation, ionizing radiation, or microwave irradiation.

26. The adhesive of claim 25, wherein the ionizing radiation comprises gamma rays or X-rays.

27. The substrate of claim 10, wherein the substrate comprises a metal substrate, a foil, a fiber, a tape, a piece of cloth, a device that can be implanted in a subject, or an aquatic substrate comprising coral, a marker, a beacon, an ordinance, or a material for producing an artificial reef.

* * * * *

SEQUENCE LISTING

<160> NUMBER OF SEQ ID NOS: 11

<210> SEQ ID NO 1
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Lys Val Phe Ile Val Leu Ala Leu Val Ser Ala Ala Tyr Gly Cys
1               5                   10                  15

Gly Val Gly Ile Gly Cys Ala Gly Gly Arg Cys Gly Gly Ala Cys Gly
            20                  25                  30

Gly Lys Gly Tyr Gly Tyr Gly Gly Lys Leu Gly Tyr Gly Ala Tyr Gly
        35                  40                  45

Lys Gly Gly Ile Gly Gly Tyr Gly Tyr Gly Lys Gly Cys Val Gly Gly
    50                  55                  60

Tyr Gly Tyr Gly Gly Leu Gly Ala Gly Lys Leu Gly Tyr Gly Tyr
65                  70                  75                  80

Gly Gly Ser Lys Cys Gly Gly Tyr Gly Tyr Gly Gly Gln Lys Leu Gly
                85                  90                  95

Gly Tyr Gly Tyr Gly Gly Lys Lys Leu Gly Gly Tyr Gly Tyr Ala Ala
            100                 105                 110

Lys Lys Val Gly Gly Tyr Gly Tyr Gly Ala Lys Lys Val Gly Gly Tyr
        115                 120                 125

Gly Tyr Gly Ala Lys Lys Val Gly Gly Tyr Gly Tyr Gly Ala Lys Lys
    130                 135                 140

Val Gly Gly Tyr Gly Tyr Gly Ala Lys Lys Val Gly Gly Tyr Gly Tyr
145                 150                 155                 160

```
Gly Ala Lys Lys Val Gly Gly Tyr Gly Tyr Gly Ala Lys Lys Val Gly
                165                 170                 175

Gly Tyr Gly Tyr Gly Val Lys Val Gly Gly Tyr Gly Tyr Gly
        180                 185                 190

<210> SEQ ID NO 2
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Val Leu Ile Phe Leu Ala Thr Val Ala Ala Val Tyr Gly Cys
1               5                   10                  15

Gly Gly Gly Gly Trp Arg Ser Gly Ser Cys Gly Gly Arg Trp Gly His
                20                  25                  30

Pro Ala Val His Lys Ala Leu Gly Gly Tyr Gly Gly Met Gly Ala His
            35                  40                  45

Pro Ala Val His Ala Ala Val His Lys Ala Leu Gly Gly Tyr Gly Ala
        50                  55                  60

Gly Ala Tyr Gly Ala Gly Ala Trp Gly His Pro Ala Val His Lys Ala
65                  70                  75                  80

Leu Gly Gly Tyr Gly Ala Gly Ala Trp Gly His Pro Ala Val His Lys
                85                  90                  95

Ala Leu Gly Gly Tyr Gly Gly Tyr Gly Ala His Pro Ala Val His Val
            100                 105                 110

Ala Val His Lys Ala Leu Gly Gly Tyr Gly Ala Gly Ala Cys Gly His
        115                 120                 125

Lys Thr Gly Gly Tyr Gly Gly Tyr Gly Ala His Pro Val Ala Val Lys
130                 135                 140

Ala Ala Tyr Asn His Gly Phe Asn Tyr Gly Ala Asn Asn Ala Ile Lys
145                 150                 155                 160

Ser Thr Lys Arg Phe Gly Gly Tyr Gly Ala His Pro Val Val Lys Lys
                165                 170                 175

Ala Phe Ser Arg Gly Leu Ser His Gly Ala Tyr Ala Gly Ser Lys Ala
            180                 185                 190

Ala Thr Gly Tyr Gly Tyr Gly Ser Gly Lys Ala Ala Gly Gly Tyr Gly
        195                 200                 205

Tyr

<210> SEQ ID NO 3
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Lys Leu Leu Ser Val Phe Ala Ile Val Val Leu Ala Val Tyr Ile
1               5                   10                  15

Thr His Val Glu Ala Asp Ser Ser Ser Ser Thr Ser Ser Ser Ser Ser
            20                  25                  30

Ser Tyr Ser Ser Ser Ser Ser Ser Ser Ser Ser Ser Ser Ser Ser Tyr
        35                  40                  45

Ser Ser Ser Ser Ser Tyr Ser Ser Ser Ser Ser Ser Tyr Ser Ser
```

```
                 50                  55                  60
Ser Ser Ser Tyr Ser Ser Ser Ser Tyr Ser Ser Ser Tyr Ser
 65                  70                  75                  80

Ser Ser Ser Tyr Ser Ser Ser Tyr Ser Ser Ser Ile Leu Thr
                 85                  90                  95

Ser Thr Ser Ser Ser Asp Trp Lys Arg Lys Val Pro Ala Arg Arg Val
                100                 105                 110

Leu Arg Thr Arg Arg Phe Leu Lys Cys Val Thr Arg Cys Thr Leu Arg
            115                 120                 125

Cys Thr Leu Phe Arg Ser Ala Lys Thr Cys Ala Arg Lys Cys Ser Arg
            130                 135                 140

Arg Cys Leu Lys Arg Val Phe
145                 150

<210> SEQ ID NO 4
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Ser Phe Thr Ile Phe Ala Ala Ile Leu Val Ala Leu Cys Tyr
 1               5                  10                  15

Ile Gln Ile Ser Glu Ala Gly Cys Cys Lys Arg Tyr Ser Ser Ser Ser
                20                  25                  30

Tyr Ser Ser Ser Ser Ser Ser Ser Ser Tyr Ser Ser Ser Ser
            35                  40                  45

Ser Ser Ser Ser Tyr Ser Ser Ser Ser Ser Tyr Ser Ser Ser Tyr Ser
 50                  55                  60

Ser Ser Ser Ser Ser Ser Ser Tyr Ser Ser Ser Ser Ser
 65                  70                  75                  80

Tyr Ser Ser Ser Ser Ser Ser Tyr Ser Ser Ser Ser Ser
                85                  90                  95

Ser Ser Ser Tyr Ser Ser Ser Ser Ser Tyr Ser Ser Ser Ser
                100                 105                 110

Ser Ser Ser Ser Tyr Ser Ser Ser Ser Ser Ser Tyr Ser
            115                 120                 125

Ser Ser Ser Ser Ser Ser Ser Tyr Ser Ser Ser Ser Ser
            130                 135                 140

Tyr Ser Ser Ser Ser Ser Ser Tyr Ser Ser Ser Ser Ser Ser
145                 150                 155                 160

Ser Ser Ser Tyr Ser Ser Ser Ser Ser Tyr Ser Ser Ser Ser
                165                 170                 175

Ser Ser Ser Ser Tyr Ser Ser Ser Ser Ser Ser Tyr Ser
            180                 185                 190

Ser Ser Ser Ser Ser Tyr Ser Ser Ser Ser Ser Tyr Ser Ser
            195                 200                 205

Ser Ser Ser Ser Ser Ser Ser Tyr Ser Ser Ser Ser Ser
            210                 215                 220

Ser Ser Ser Ser Tyr Ser Ser Ser Ser Ser Tyr Ser Ser Ser
225                 230                 235                 240

Ser Ser Ser Ser Ser Tyr Ser Ser Ser Ser Ser Ser Ser Tyr
                245                 250                 255
```

```
Ser Ser Ser Ser Ser Ser Ser Ser Ser Tyr Ser Ser Ser Ser
            260                 265                 270

Ser Ser Ser Ser Ser Tyr Ser Ser Ser Ser Ser Tyr Ser Ser
        275                 280                 285

Ser Ser Ser Ser Ser Tyr Ser Ser Ser Ser Ser Ser Ser Ser
    290                 295                 300

Tyr Ser Ser Ser Ser Ser Ser Tyr Ser Ser Ser Ser Ser Ser Ser Ser
305                 310                 315                 320

Ser Ser Ser Ser Tyr Ser Ser Ser Ser Ser Ser Ser Ser Ser
            325                 330                 335

Ser Ser Ser Ser Ser Ser
        340

<210> SEQ ID NO 5
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Pro Thr Leu Tyr Lys Lys Val Gly Lys Leu Val Ile Leu Ala Ile
1               5                   10                  15

Ile Val Thr Val Ala Ser Val Ala Ser Ala Gly Tyr Pro Thr Tyr Ser
            20                  25                  30

Pro Ser Gly Gly Thr His Ser Gly Tyr Asn Gly Pro His Gly Asn Val
        35                  40                  45

Val Lys Lys Thr Tyr Arg Gly Pro Tyr Gly Ala Gly Ala Ala Lys Ala
    50                  55                  60

Trp Asn Gly Tyr His Gly Ala Gly Tyr Thr Ser Val His His Gly Pro
65                  70                  75                  80

Ala Ser Thr Ser Trp His Thr Ser Trp Ser Asn Lys Lys Gly Gly Tyr
                85                  90                  95

Gly Tyr Gly Leu Lys Asn Lys Gly Tyr Gly Tyr Gly Leu Lys Lys Val
            100                 105                 110

Gly Tyr Gly Val Gly Leu His Ala Ala Gly Trp His Gly Val Gly Pro
        115                 120                 125

Tyr Gly Ala Gly Tyr His Gly Ala Gly Trp Asn Gly Leu Gly Tyr His
    130                 135                 140

Gly Ala Gly Tyr Gly Val His Gly Val Gly Leu His Gly Ala Gly Tyr
145                 150                 155                 160

Gly Leu His Gly Val Gly Leu His Gly Ala Gly Val Gly Leu His Gly
                165                 170                 175

Val Gly Leu His Gly Ala Gly Tyr Gly Leu His Gly Val Gly Leu His
            180                 185                 190

Gly Ala Gly Tyr Gly Leu His Gly Val Gly Leu His Gly Ala Gly Tyr
        195                 200                 205

Gly Leu His Gly Val Gly Leu His Gly Ala Gly Tyr Gly Leu His Gly
    210                 215                 220

Val Gly Leu His Gly Ala Gly Tyr Gly Leu His Gly Val Gly Leu His
225                 230                 235                 240

Gly Ala Gly Tyr Gly Leu His Gly Val Gly Leu His Gly Ala Gly Cys
                245                 250                 255

Gly Ile His Lys Thr Ala Cys Tyr Gly Val Gly Leu His Gly His Tyr
            260                 265                 270
```

<210> SEQ ID NO 6
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Lys Phe Leu Val Leu Leu Ala Leu Val Ala Ser Ala Ser Ala Tyr
1               5                   10                  15

Tyr Pro Leu Met Gly Gly Phe His Gly Gly Trp His Ala Pro Met Val
                20                  25                  30

His Gly Gly Leu Tyr His Gly Gly Trp His Ala Pro Met Val His Gly
            35                  40                  45

Gly Leu Tyr His Gly Gly Trp His Ala Pro Ile Val His Gly Gly Trp
        50                  55                  60

His Ala Pro Val Phe His Ala Pro Ala Pro Ile His Thr Val Ser His
65                  70                  75                  80

Ser Val Val Asn His Val Pro Met Met Pro Met Trp His His Pro Ala
                85                  90                  95

Pro Ala Pro Ala Pro Ala Pro Arg Pro Gly Arg Ile Ile Ile Leu Gly
                100                 105                 110

Gly Gly Lys Tyr Gly Pro Phe Gly Lys Tyr Gly Gly Ala Gly Leu
            115                 120                 125

Leu Ala Leu Gly Ala Leu Gly Gly Asn Gly Gly Phe Trp Lys Arg Arg
130                 135                 140

<210> SEQ ID NO 7
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Thr Leu Phe Tyr Asn Ala Asn Phe Val Gln Lys Ser Trp Val
1               5                   10                  15

Leu Ile Leu Leu Gly Leu Ala Ala Val Val Ala Cys Ser Glu Tyr Asp
                20                  25                  30

Lys Gly Leu Gly Gly Tyr Gly Arg Pro Ser Tyr Gly Gly Arg Arg Gly
            35                  40                  45

Tyr Gly Gly Arg Arg Gly Leu Gln Tyr His Gly Lys Tyr Gln Gly Arg
        50                  55                  60

Cys Glu Tyr Asp Gly Leu Tyr Phe Arg Asp Glu Lys Ser Phe Val Tyr
65                  70                  75                  80

Cys Ser Asn Arg Asn Ser Tyr Ile Gln Pro Cys Ala Pro Gly Thr Arg
                85                  90                  95

Asn Ser Pro Tyr Thr Lys Tyr Asn Arg Gly Ser Lys Tyr Asn Tyr Arg
                100                 105                 110

Asp Phe Cys Glu Phe Asn Leu Val Asp Ser Gly Tyr Val Pro Lys Pro
            115                 120                 125

Gly Tyr Leu Pro Ala Pro Lys Lys Ala Tyr Pro Thr Lys Val Tyr Asp
        130                 135                 140

Leu Lys Val Asp Tyr Ala Pro Lys Val Asp Tyr Ala Pro Lys Val Asp
145                 150                 155                 160

Tyr Ala Pro Lys Val Asp Tyr Pro Lys Val Asp Tyr Ala Pro Lys
            165                 170                 175

Ala Ser Val Val Pro Pro Lys Ala Ser Tyr Val Asp Pro Thr Pro Thr
            180                 185                 190

Tyr Gly Tyr Glu Ala Pro Phe Lys Gly Gly Tyr Asp Lys Pro Ser Tyr
            195                 200                 205

Gly Lys Asp Val Asp Thr Ser Tyr Glu Ser Lys Thr Thr Tyr Thr Val
210                 215                 220

Glu Lys Thr Ala Asp Lys Gly Tyr Gly Lys Gly Tyr Gly Asp Lys Glu
225                 230                 235                 240

Ile Ser Ala Lys Lys Ser Tyr Thr Leu Thr Glu Lys Arg Asp Tyr Asp
            245                 250                 255

Thr Gly Tyr Asp Asn Ser Arg Ser Asp Glu Asp Ser Lys Glu Tyr Gly
            260                 265                 270

Tyr Asp Asn Asp Arg Ser Glu Ser Tyr Glu Arg Thr Glu Ser Tyr Thr
            275                 280                 285

Asp Glu Arg Thr Asp Gly Tyr Gly Thr Gln Lys Val Glu Tyr Thr Gln
            290                 295                 300

Gln Ser Glu Tyr Asp Arg Val Thr Arg Arg Gly Ile Trp Leu His Lys
305                 310                 315                 320

Gly Thr Glu Val Glu His Val Leu Tyr
            325

<210> SEQ ID NO 8
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (49)..(49)
<223> OTHER INFORMATION: Any amino acid

<400> SEQUENCE: 8

Met Asn Thr Phe Val Val Ile Ala Ala Ile Val Ala Val Ala Ala Cys
1               5                   10                  15

Ser Gly Gly Tyr Asp Gly Arg Gln Tyr Thr Tyr Arg Gly Arg Tyr Asn
            20                  25                  30

Asn Lys Cys Gly Asn Asp Gly Leu Tyr Phe Lys Asp Asp Lys Asn Phe
        35                  40                  45

Xaa Phe Cys Ser Asn Gly Asn Ser Tyr Val Gln Pro Cys Ala Pro Gly
    50                  55                  60

Thr Arg Asn Ser Gly Tyr Asn Asn Tyr Lys Gln Gly Ser Ile Tyr Asn
65                  70                  75                  80

Tyr Arg Asp Phe Cys Asp Val Asn Leu Val Asp Glu Gly Tyr Gly Val
                85                  90                  95

Gly Ala Lys Pro Gly Tyr Asn Lys Gly Tyr Asn Pro Gly Tyr Asn Pro
            100                 105                 110

Gly Tyr Gly Gly Tyr Asn Pro Gly Tyr Ser Thr Gly Tyr Gly Gly Tyr
        115                 120                 125

Lys Ala Gly Pro Gly Pro Tyr Trp
    130                 135

<210> SEQ ID NO 9
<211> LENGTH: 169

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Any amino acid

<400> SEQUENCE: 9

Met Ser Asn Ala Phe Leu Xaa Cys Gln Leu Cys Thr Lys Lys Leu Ala
1               5                   10                  15

Leu Leu Leu Leu Val Ala Val Cys Ala Ala Val Ala Val Asn Ala Cys
            20                  25                  30

Gly Pro Leu Gly Cys Ser Gly Gly Tyr Gly Gly Val Leu Lys Cys Gly
        35                  40                  45

Val Gly Gly Cys Ala Leu Gly Gly Tyr Gly Gly Tyr Ser Ala Gly
    50                  55                  60

Ile Gly Gly Tyr Gly Ile Lys Arg Leu Gly Cys Arg Gly Gly Arg Cys
65                  70                  75                  80

Gly Leu Arg Arg Arg Val Gly Cys Arg Gly Arg Cys Gly Leu Arg
                85                  90                  95

Gly Arg Leu Gly Cys Arg Gly Cys Arg Cys Gly Leu Arg Lys Leu Gly
            100                 105                 110

Cys Arg Gly Gly Arg Cys Gly Leu Arg Gly Arg Leu Gly Cys Arg Gly
            115                 120                 125

Gly Arg Cys Gly Leu Arg Lys Arg Leu Gly Cys Arg Gly Gly Arg Gly
        130                 135                 140

Arg Gly Gly Tyr Gly Gly Gly Tyr Gly Gly Val Cys Ser Lys Gly Val
145                 150                 155                 160

Cys Gly Gly Tyr Pro Ala Tyr Gly Lys
                165

<210> SEQ ID NO 10
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Ser Phe Thr Ile Phe Ala Ala Ile Leu Val Ala Leu Cys Tyr
1               5                   10                  15

Ile Gln Ile Ser Glu Ala Gly Cys Cys Lys Arg Tyr Ser Ser Ser Ser
            20                  25                  30

Tyr Ser Ser Ser Ser Ser Ser Ser Ser Tyr Ser Ser Ser Ser
        35                  40                  45

Ser Ser Ser Ser Tyr Ser Ser Ser Ser Ser Ser Ser Ser Tyr Ser
    50                  55                  60

Ser Ser Ser Ser Ser Ser Ser Tyr Ser Ser Ser Ser Ser Ser
65                  70                  75                  80

Tyr Ser Ser Ser Ser Ser Ser Tyr Ser Ser Ser Ser Ser Ser
                85                  90                  95

Ser Ser Ser Tyr Ser Ser Ser Ser Ser Tyr Ser Ser Ser Ser
            100                 105                 110

Ser Ser Ser Ser Tyr Ser Ser Ser Ser Ser Ser Ser Tyr Ser
            115                 120                 125
```

```
Ser Ser Ser Ser Ser Ser Ser Ser Tyr Ser Ser Ser Ser Ser
        130                 135                 140
Tyr Ser Ser Ser Ser Ser Ser Tyr Ser Ser Ser Ser Ser Ser Ser Ser
145                 150                 155                 160
Ser Ser Ser Tyr Ser Ser Ser Ser Ser Tyr Ser Ser Ser Ser
            165                 170                 175
Ser Ser Ser Ser Tyr Ser Ser Ser Ser Ser Ser Ser Tyr Ser
                180                 185                 190
Ser Ser Ser Ser Ser Tyr Ser Ser Ser Ser Ser Tyr Ser Ser
                    195                 200                 205
Ser Ser Ser Ser Ser Ser Ser Ser Tyr Ser Ser Ser Ser Ser
        210                 215                 220
Ser Ser Ser Ser Tyr Ser Ser Ser Ser Ser Tyr Ser Ser Ser
225                 230                 235                 240
Ser Ser Ser Ser Ser Tyr Ser Ser Ser Ser Ser Ser Ser Tyr
                245                 250                 255
Ser Ser Ser Ser Ser Ser Ser Ser Tyr Ser Ser Ser Ser Ser
            260                 265                 270
Ser Ser Ser Ser Ser Tyr Ser Ser Ser Ser Ser Tyr Ser Ser
                275                 280                 285
Ser Ser Ser Ser Tyr Ser Ser Ser Ser Ser Ser Ser Ser Ser
        290                 295                 300
Tyr Ser Ser Ser Ser Ser Ser Tyr Ser Ser Ser Ser Ser Ser Ser Ser
305                 310                 315                 320
Ser Ser Ser Ser Tyr Ser Ser Ser Ser Ser Ser Ser Ser Ser
            325                 330                 335
Ser Ser Tyr Ser Ser Ser
            340

<210> SEQ ID NO 11
<211> LENGTH: 272
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Pro Thr Leu Tyr Lys Lys Val Gly Lys Leu Val Ile Leu Ala Ile
1               5                   10                  15
Ile Val Thr Val Ala Ser Val Ala Ser Ala Gly Tyr Pro Thr Tyr Ser
                20                  25                  30
Pro Ser Gly Gly Thr His Ser Gly Tyr Asn Gly Pro His Gly Asn Val
            35                  40                  45
Val Lys Lys Thr Tyr Arg Gly Pro Tyr Gly Ala Gly Ala Lys Ala
        50                  55                  60
Trp Asn Gly Tyr His Gly Ala Gly Tyr Thr Ser Val His His Gly Pro
65                  70                  75                  80
Ala Ser Thr Ser Trp His Thr Ser Trp Ser Asn Lys Lys Gly Gly Tyr
                85                  90                  95
Gly Tyr Gly Leu Lys Asn Lys Gly Tyr Gly Tyr Gly Leu Lys Lys Val
                100                 105                 110
Gly Tyr Gly Val Gly Leu His Ala Ala Gly Trp His Gly Val Gly Pro
            115                 120                 125
Tyr Gly Ala Gly Tyr His Gly Ala Gly Trp Asn Gly Leu Gly Tyr His
```

```
                130                 135                 140
Gly Ala Gly Tyr Gly Val His Gly Val Gly Leu His Gly Ala Gly Tyr
145                 150                 155                 160

Gly Leu His Gly Val Gly Leu His Gly Val Gly Tyr Gly Leu His Gly
                165                 170                 175

Val Gly Leu His Gly Ala Gly Tyr Gly Leu His Gly Val Gly Leu His
            180                 185                 190

Gly Val Gly Tyr Gly Leu His Gly Val Gly Leu His Gly Ala Gly Tyr
        195                 200                 205

Gly Ile His Gly Val Gly Leu His Gly Val Gly Tyr Gly Leu His Gly
    210                 215                 220

Val Gly Leu His Gly Ala Gly Tyr Gly Leu His Gly Val Gly Leu His
225                 230                 235                 240

Gly Val Gly Tyr Gly Leu His Gly Val Gly Leu His Gly Ala Gly Cys
                245                 250                 255

Gly Ile His Lys Thr Ala Cys Tyr Gly Val Gly Leu His Gly His Tyr
            260                 265                 270
```